(12) United States Patent
Fujikawa et al.

(10) Patent No.: US 8,048,049 B2
(45) Date of Patent: Nov. 1, 2011

(54) SANITARY NAPKIN

(75) Inventors: Shinobu Fujikawa, Mitoyo-gun (JP);
Toshiyuki Tanio, Mitoyo-gun (JP);
Kenichiro Kuroda, Mitoyo-gun (JP);
Wataru Yoshimasa, Mitoyo-gun (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 68 days.

(21) Appl. No.: 11/293,734

(22) Filed: Dec. 1, 2005

(65) Prior Publication Data
US 2006/0142725 A1 Jun. 29, 2006

(30) Foreign Application Priority Data
Dec. 28, 2004 (JP) .................. 2004-379832

(51) Int. Cl.
*A61F 13/15* (2006.01)
*A61F 13/20* (2006.01)
(52) U.S. Cl. ........ 604/385.01; 604/385.24; 604/385.101
(58) Field of Classification Search ........... 604/385.101, 604/385.24–385.3, 385.17, 387
See application file for complete search history.

(56) References Cited

U.S. PATENT DOCUMENTS

| | | | |
|---|---|---|---|
| 4,804,380 A | | 2/1989 | Lassen et al. |
| 4,808,177 A * | | 2/1989 | DesMarais et al. ...... 604/385.27 |
| 5,324,278 A * | | 6/1994 | Visscher et al. ......... 604/385.04 |
| H1614 H * | | 11/1996 | Mayer et al. ............. 604/385.23 |
| H1634 H * | | 2/1997 | Oetjen et al. ............. 604/385.23 |
| 5,746,732 A * | | 5/1998 | Olsson et al. ............ 604/385.28 |
| 5,853,403 A * | | 12/1998 | Tanzer et al. ............ 604/385.09 |
| 5,899,894 A * | | 5/1999 | Palumbo et al. ............... 604/378 |
| 5,906,603 A * | | 5/1999 | Roe et al. ................. 604/385.24 |
| 6,126,648 A * | | 10/2000 | Keck et al. ............... 604/385.24 |
| 6,293,935 B1 * | | 9/2001 | Kimura et al. ................ 604/387 |
| 6,410,822 B1 * | | 6/2002 | Mizutani ...................... 604/380 |
| 6,413,248 B1 | | 7/2002 | Mizutani |
| 6,471,682 B2 * | | 10/2002 | Kashiwagi ............... 604/385.27 |
| 6,676,649 B2 * | | 1/2004 | Mizutani ....................... 604/387 |
| 2002/0120247 A1* | | 8/2002 | Mizutani et al. ......... 604/385.17 |
| 2002/0156450 A1* | | 10/2002 | Drevik et al. .......... 604/385.101 |
| 2003/0055392 A1 | | 3/2003 | Tagami et al. |
| 2003/0088222 A1* | | 5/2003 | Yoshimasa et al. ........... 604/380 |
| 2004/0147891 A1* | | 7/2004 | Sugito et al. ............ 604/385.01 |
| 2005/0124951 A1 | | 6/2005 | Kudo et al. |

(Continued)

FOREIGN PATENT DOCUMENTS
CN 1408330 4/2003
(Continued)

OTHER PUBLICATIONS

Merriam-Webster OnLine definitions of "hollow".*
(Continued)

*Primary Examiner* — Tatyana Zalukaeva
*Assistant Examiner* — Susan Su
(74) *Attorney, Agent, or Firm* — Morrison & Foerster LLP

(57) ABSTRACT

A sanitary napkin includes a napkin body having a liquid-absorbent layer for absorbing and retaining liquid and a projection projecting from a body surface of the napkin body. The projection is secured at laterally spaced base ends to the body surface of the napkin body. A distance between the base ends varies longitudinally of the projection. A height of the projection from the body surface of the napkin body decreases with increasing the distance between the base ends.

8 Claims, 16 Drawing Sheets

U.S. PATENT DOCUMENTS

| | | | |
|---|---|---|---|
| 2007/0005036 A1* | 1/2007 | Nishikawa et al. | 604/380 |
| 2007/0073253 A1* | 3/2007 | Miyama et al. | 604/380 |
| 2007/0118090 A1* | 5/2007 | Kawamura | 604/385.101 |

FOREIGN PATENT DOCUMENTS

| | | |
|---|---|---|
| EP | 0 335 253 A1 | 10/1989 |
| EP | 985395 A2 * | 3/2000 |
| EP | 0985396 A2 * | 3/2000 |
| JP | 64-70051 A | 3/1989 |
| JP | 2-11139 A | 1/1990 |
| JP | 9-506806 A | 7/1997 |
| JP | 9-508548 A | 9/1997 |
| JP | 09-313529 A | 12/1997 |
| JP | 11-042250 A | 2/1999 |
| JP | 11-513921 A | 11/1999 |
| JP | 2000-264 | 1/2000 |
| JP | 2000-083994 A | 3/2000 |
| JP | 2001-504727 A | 4/2001 |
| JP | 2001-245921 | 9/2001 |
| JP | 2002-301097 A | 10/2002 |
| JP | 2002-320638 A | 11/2002 |
| JP | 2003-093442 A | 4/2003 |
| JP | 2004-181085 A | 7/2004 |
| WO | WO-95/17150 A2 | 6/1995 |
| WO | WO-95/20932 A1 | 8/1995 |
| WO | WO 9745082 A1 * | 12/1997 |
| WO | WO-98/00085 A1 | 1/1998 |
| WO | WO-98/22060 A1 | 5/1998 |
| WO | WO-02/087483 A1 | 11/2002 |
| WO | WO-03/053301 | 7/2003 |

OTHER PUBLICATIONS

Definition of "resilient", Merriam Webster OnLine.*
Chinese Office Action mailed Apr. 27, 2010 directed to CN-200580044967.9; 10 pages.
Japanese Notification of Reasons for Refusal mailed Aug. 17, 2010, directed to corresponding Japanese Application No. 2004-379832; 6 pages.
Japanese Notification of Reasons for Refusal mailed Nov. 16, 2010, directed to counterpart Japanese Application No. JP-2004-379832; 6 pages.

* cited by examiner

SANITARY NAPKIN

INCORPORATION BY REFERENCE

The present application claims priority under 35 U.S.C. §119 to Japanese Patent Application No. 2004-379832 filed on Dec. 28, 2004 in the Japanese language, which is hereby incorporated by reference in its entirety.

BACKGROUND OF THE INVENTION

1. Field of the Invention

The present invention relates to a sanitary napkin with a projection disposed on a body surface of a napkin body and more particularly to a sanitary napkin whose projection can easily conform to the contours of the woman's body so as to be effective in preventing leakage of menstrual blood.

2. Description of the Related Art

There have been known sanitary napkins with a napkin body containing a liquid-absorbent layer and a projection projecting from a body surface of the napkin body.

Japanese Unexamined Patent Application Publication No. H11-513921 discloses a sanitary napkin in which a primary absorbent component having a generally triangular cross section is disposed on a body surface of a secondary absorbent component. The primary absorbent component is constructed by wrapping a hydrophilic foam structure in an outer cover. The cross-sectional shape of the primary absorbent component does not change over the length of the sanitary napkin.

Japanese Unexamined Patent Application Publication No. H09-313529 discloses a sanitary napkin whose upper surface layer is centrally folded to form a jetty. This jetty has longitudinally-extending elastic members in its right and left side portions and is raised from the body surface of the napkin body under elastic tension exerted by the elastic members. The jetty extends longitudinally of the sanitary napkin with a uniform width.

Japanese Unexamined Patent Application Publication No. 2002-320638 discloses a sanitary napkin in which a T-section three-dimensional wall formed of a liquid-permeable sheet is disposed on the body surface of the napkin body. This three-dimensional wall has elastic members for exerting a longitudinal contractive force and is raised from the body surface of the napkin body when the napkin body is curved with front and rear edges of the napkin body being drawn closer to each other by the elastic members. The width of the three-dimensional wall does not change over the length of the napkin body.

Japanese Unexamined Patent Application Publication No. 2001-504727 discloses a sanitary napkin which has a liquid-absorbent layer and a topsheet disposed on a body surface of the liquid-absorbent layer with an absorbent body and a stiffening element interposed between the liquid-absorbent layer and the topsheet. The topsheet, the absorbent body, and the stiffening element form a hump having a generally triangular cross section. In the hump, both the width and height gradually increases from the front end to the center and gradually decreases from the center to the rear end.

In all these conventional sanitary napkins, a projection designed to fit against the wearer's body is disposed on the body surface of the napkin body so as to prevent leakage of liquid such as menstrual blood.

In the woman's crotch, however, the cleft varies in shape anteroposteriorly to have different opening widths and depths for different regions. Around the vaginal opening and the labia majora, the cleft has a relatively large opening width. Near and behind the anus, the cleft lies between the buttocks. The cleft between the buttocks (or the intergluteal cleft) becomes the deepest behind the anus and then shallower toward the coccyx.

Moreover, in order that the liquid absorbent layer of the sanitary napkin can effectively absorb liquid such as menstrual blood discharged from the vaginal opening, the sanitary napkin should reliably fit on the vaginal opening and its vicinity.

In the sanitary napkins disclosed in the Patent Publication Nos. H11-513921, H09-313529, and 2002-320638, however, the projection is uniform in width and does not change much in height over the length of the projection. Therefore, the projection, which is not in conformity with the contours of the woman's crotch, may cause a problem of failing to snugly fit on the vaginal opening or to reliably find its way into the intergluteal cleft.

In the sanitary napkin disclosed in the Patent Publication No. 2001-504727, on the other hand, both the width and the height become the largest centrally of the projection. When the center of the projection is applied to the vaginal opening and its vicinity, the projection tends to make a wearer feel uncomfortable because it is too high. When the center of the projection is applied to the intergluteal cleft, the projection cannot easily find its way into the intergluteal cleft because it is too wide. When the center of the projection is applied to the coccyx and its vicinity, the projection tends to create a gap between the napkin body and the buttocks because it is too high.

SUMMARY OF THE INVENTION

The present invention has been developed to solve the problems in the prior art set forth above and has an object to provide a sanitary napkin in which a projection varies in width and height in accordance with the physical features of a woman so as to improve conformity with the body of a woman.

According to a first aspect of the present invention, there is provided a sanitary napkin comprising:

a napkin body having a liquid-absorbent layer for absorbing and retaining liquid; and a projection projecting from a body surface of the napkin body, wherein the projection is secured at laterally spaced base ends to the body surface of the napkin body, a distance between the base ends varies longitudinally of the projection, and a height of the projection from the body surface of the napkin body decreases with increasing the distance between the base ends.

In this construction, accordingly, the projection is relatively low at a portion where the width of the projection is relatively large and relatively high at a location where the width of the projection is relatively small. The relatively high, narrow portion can easily fit in a deep portion of the intergluteal cleft; the relatively low, wide portion can easily fit on the vaginal opening and its vicinity, in a rear shallow portion of the intergluteal cleft, or on the coccyx and its vicinity.

Preferably, the distance between the base ends is larger in a front portion of the projection than in a rear portion behind the front portion. In this construction, the front portion of the projection can easily fit on the vaginal opening and its vicinity, and the rear portion can easily fit in a deep portion of the intergluteal cleft.

Also preferably, the distance between the base ends is larger in front and rear portions of the projection than in an intermediate portion between the front and rear portions. In this construction, the front portion of the projection can easily fit on the vaginal opening and its vicinity, the intermediate portion of the projection can easily fit in a deep portion of the intergluteal cleft, and the rear portion of the projection can easily fit in a rear shallow portion of the intergluteal cleft or on the coccyx and its vicinity.

Here, the distance between the base ends may vary stepwise or continuously.

In the first aspect of the present invention, the projection may be adapted to exert a longitudinal elastic contractive force to draw front and rear ends of the napkin body closer to each other and concavely curve the body surface of the napkin body, so that the projection can be raised from the body surface of the napkin body.

In the first aspect of the present invention, the projection may be formed separately from the napkin body and then secured on the body surface of the napkin body. Alternatively, the napkin body may include a topsheet covering the liquid-absorbent layer, and the protrusion may be formed by a part of the topsheet.

According to the present invention, the projection can easily conform to the contours of the woman's body. Thus, lateral leakage or rearward leakage of liquid such as menstrual blood can be effectively prevented.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
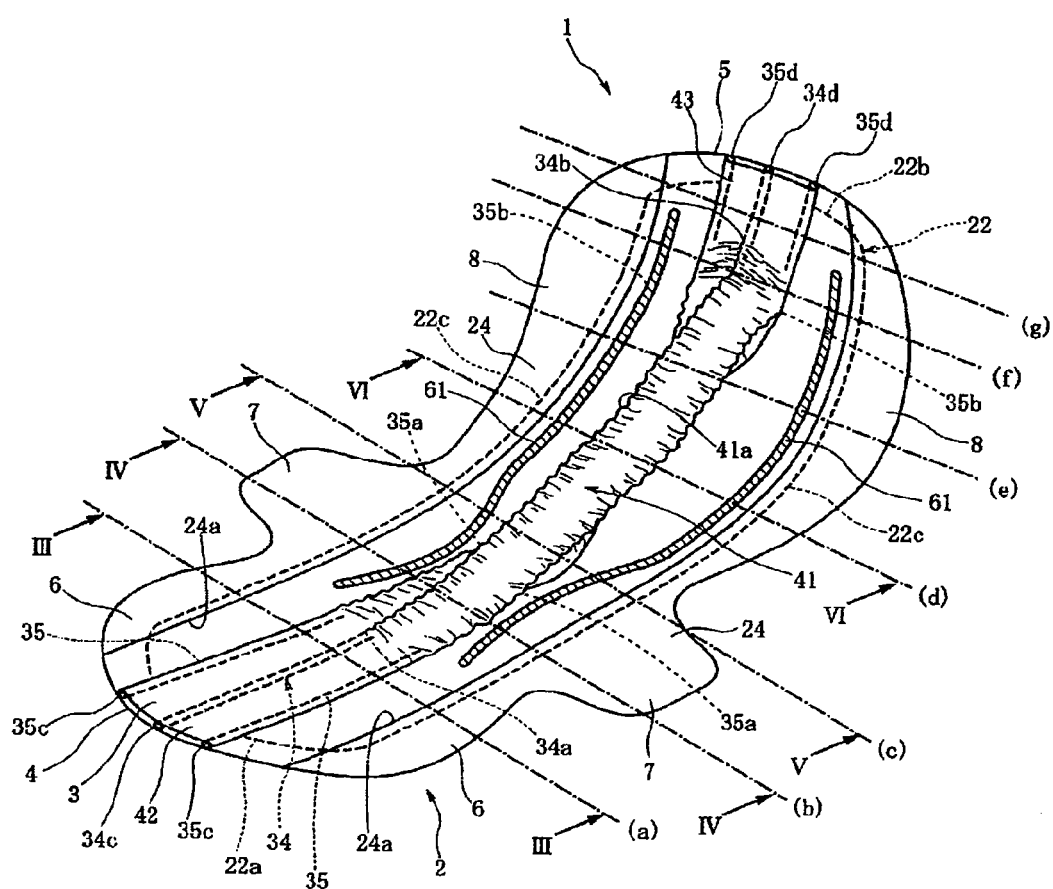
FIG. 1 is a perspective view of a sanitary napkin according to a first embodiment of the present invention in a natural state where no external force is exerted thereon.
Figure 2:
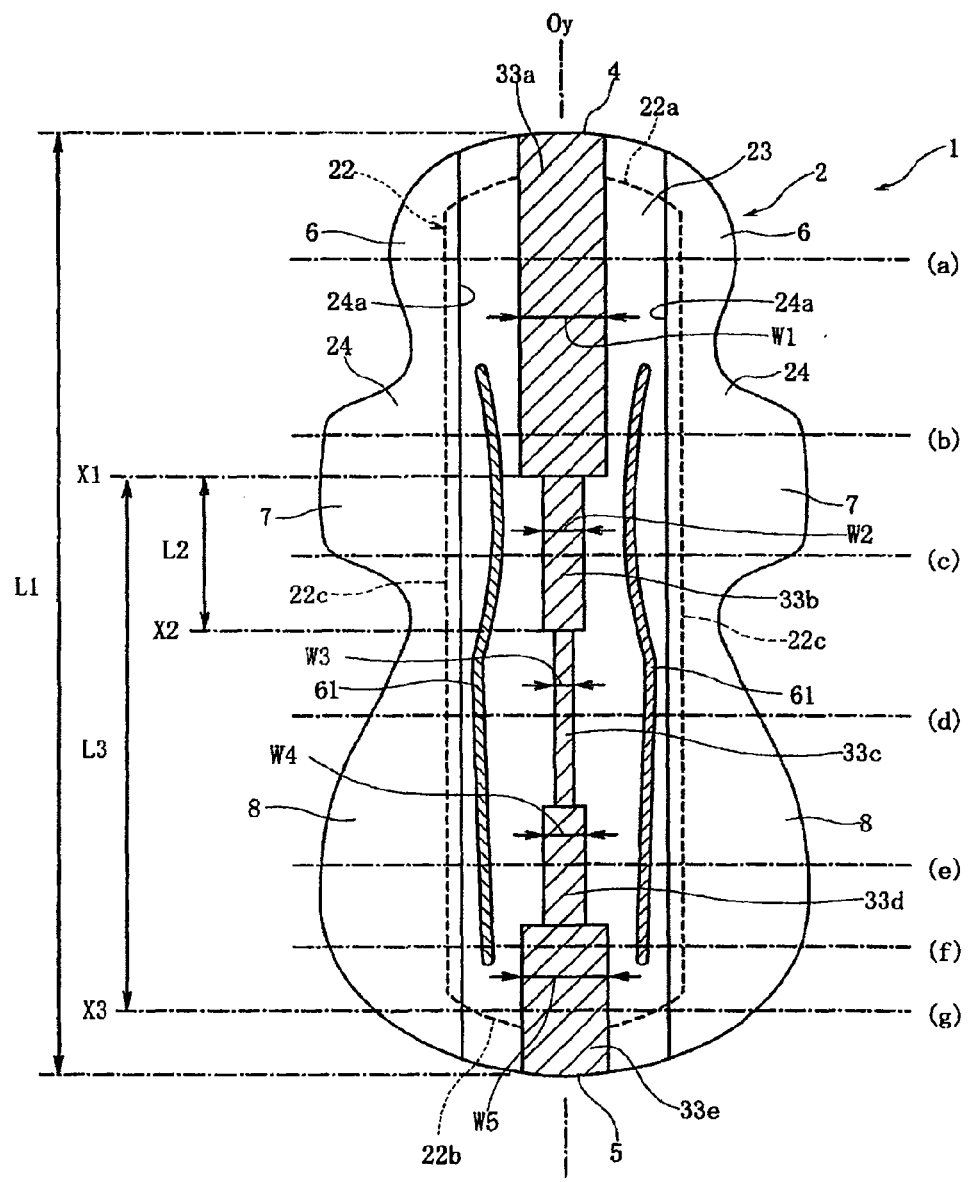
FIG. 2 is a plan view showing a body surface of a flattened napkin body according to the first embodiment.
Figure 3:
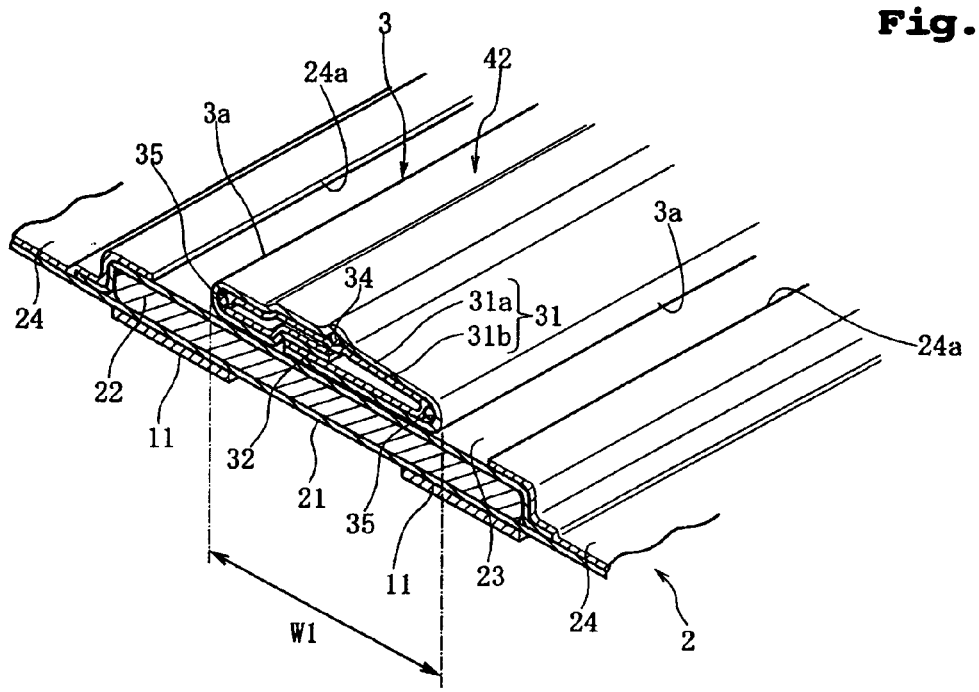
FIG. 3 is a sectional view taken along line of FIG. 1.
Figure 4:
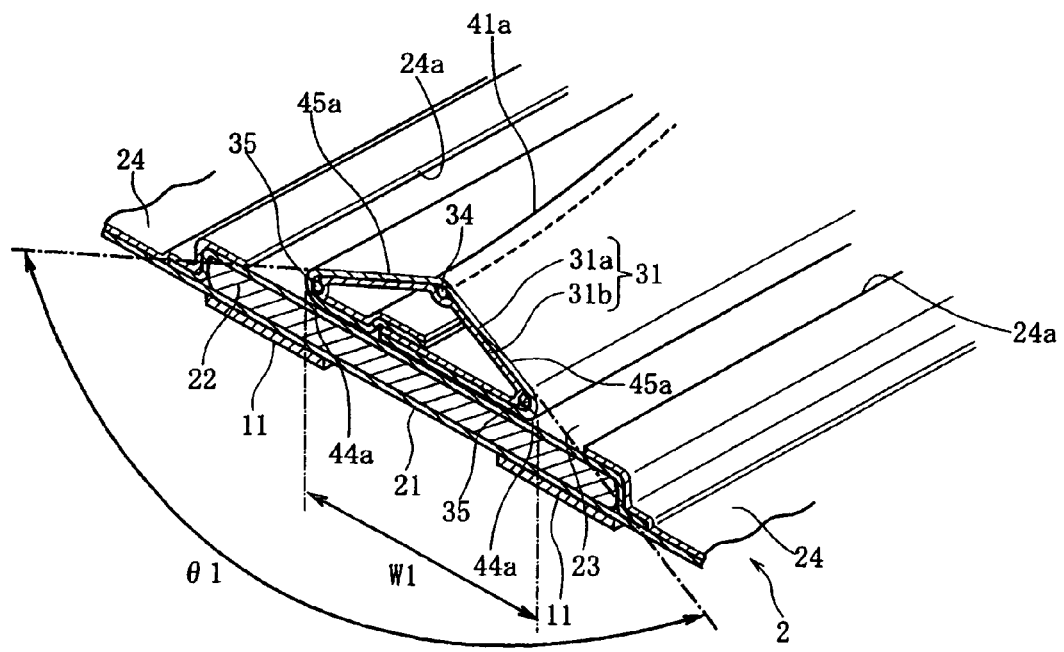
FIG. 4 is a sectional view taken along line IV-IV of FIG. 1.
Figure 5:
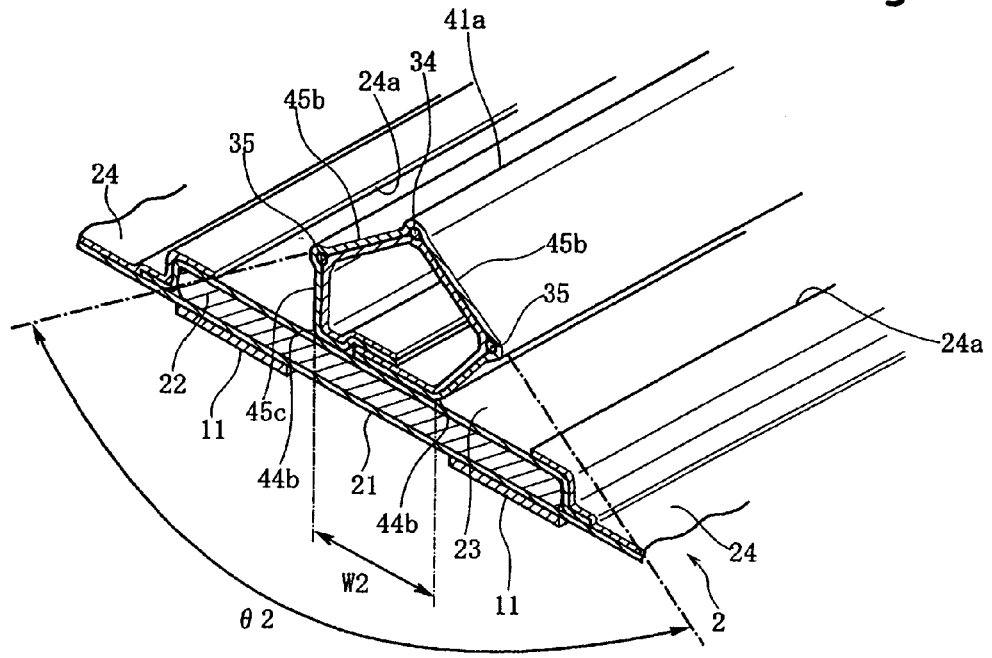
FIG. 5 is a sectional view taken along line V-V of FIG. 1.
Figure 6:
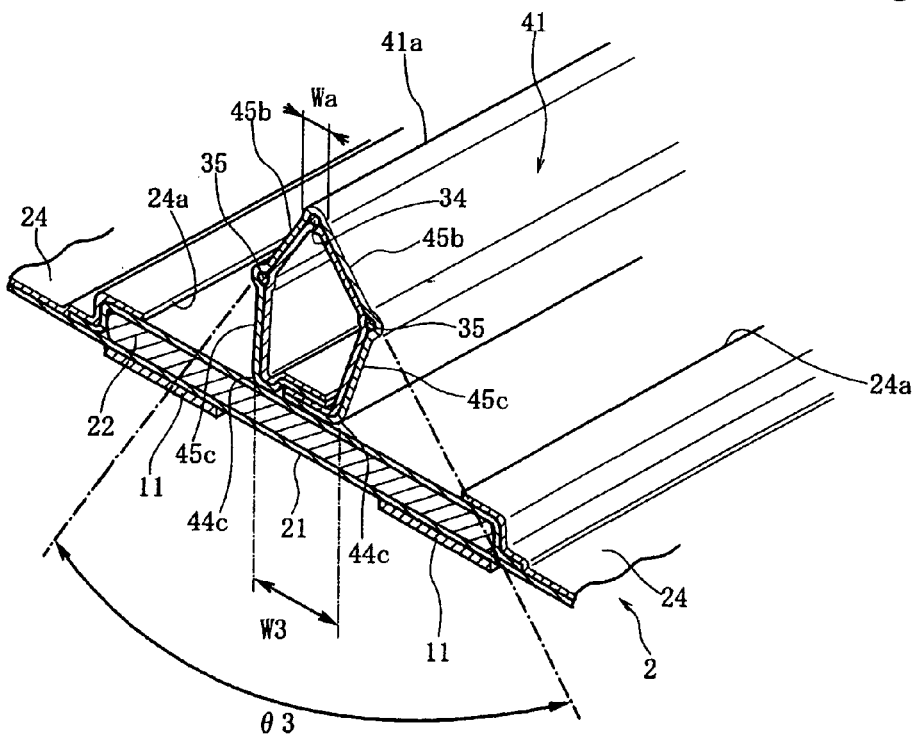
FIG. 6 is a sectional view taken along line VI-VI of FIG. 1.
Figure 7:
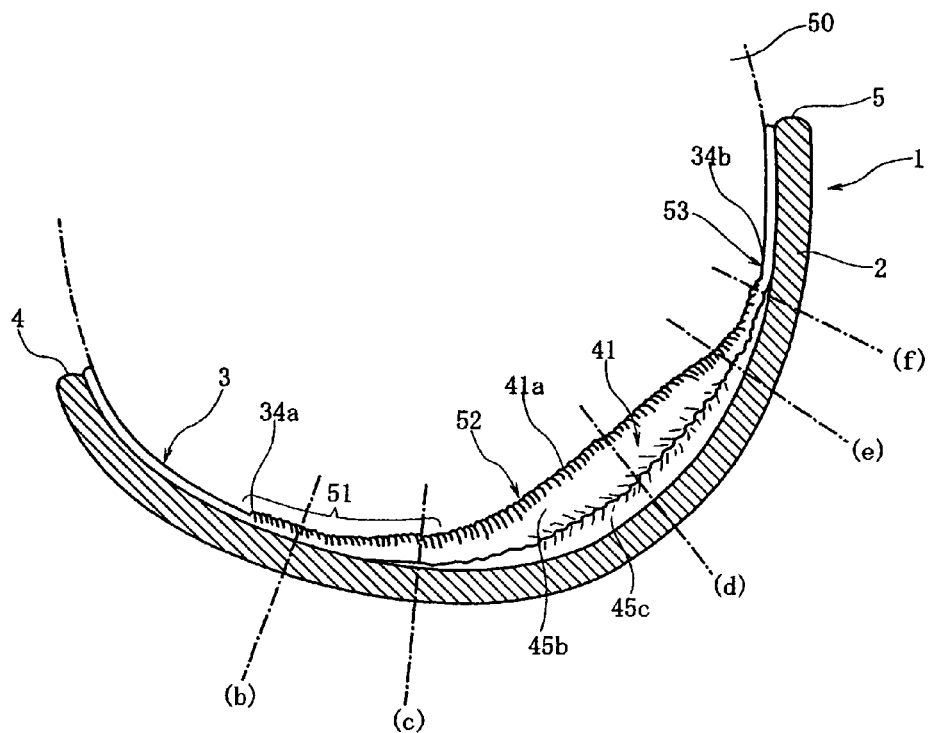
FIG. 7 is a longitudinal sectional view schematically showing a state where a sanitary napkin is applied to the woman's body.

FIG. 1 is a perspective view of a sanitary napkin 1 according to a first embodiment of the present invention in a natural state where no external force is exerted thereon. FIG. 2 is a plan view in which a surface element is removed from the sanitary napkin 1 and only a napkin body is flattened. FIG. 3 is a sectional view taken along line of FIG. 1, FIG. 4 is a sectional view taken along line IV-IV of FIG. 1, FIG. 5 is a sectional view taken along line V-V of FIG. 1, and FIG. 6 is a sectional view taken along line VI-VI of FIG. 1. FIG. 7 is a longitudinal sectional view schematically showing a state where the sanitary napkin 1 is applied to the woman's body from the crotch to the buttocks.

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width".

In FIG. 1, several locations, which are spaced apart from each other in the longitudinal direction of the sanitary napkin 1, are indicated by (a) to (g). Also in FIG. 2, the corresponding locations are indicated by (a) to (g).

The sanitary napkin 1 comprises a napkin body 2 and a surface element 3 disposed on the body surface of the napkin body 2 to form a projection.

As shown in FIGS. 3 to 6, the napkin body 2 includes a liquid-blocking backsheet 21 on the garment surface side of the napkin body 2, a liquid-absorbent layer 22 disposed on the backsheet 21, and a liquid-permeable topsheet 23 covering the liquid-absorbent layer 22.

As shown in FIG. 2, the napkin body 2 has arcuate front and rear edges 4, 5. The napkin body 2 is elongated to have a length L1 in the range of 280 to 450 mm. The liquid-absorbent layer 22 is also elongated to have arcuate front and rear edges 22a, 22b, which are spaced slightly inward from the front and rear edges 4, 5, respectively. Furthermore, the liquid-absorbent layer 22 has right and left side edges 22c, 22c, which extend linearly in parallel to a longitudinal centerline Oy. However, the shape of the right and left side edges 22c, 22c of the liquid-absorbent layer 22 should not be understood as limited to this embodiment.

On laterally opposite sides of the liquid-absorbent layer 22, the napkin body 2 has laterally projecting front flaps 6, 6, laterally projecting fold-back flaps 7, 7, and laterally projecting rear flaps 8, 8 in order from front to rear. In the front flaps 6, 6, the fold-back flaps 7, 7, and the rear flaps 8, 8, the body surface of the backsheet 21 is covered with a liquid-blocking side sheet 24. The liquid-blocking side sheet 24 is bonded to the backsheet 21 through a hot-melt type adhesive.

As shown in FIGS. 3 to 6, the side sheets 24, 24 lie opposite one another with their opposing edges 24a, 24a located inside the side edges 22c, 22c of the liquid-absorbent layer 22 (i.e., located closer to the longitudinal centerline Oy than the side edges 22c, 22c). At the laterally opposite side portions of the liquid-absorbent layer 22, therefore, the body surface of the liquid-absorbent layer 22 is covered with the topsheet 23, and the body surface of the topsheet 23 is further covered with the side sheets 24, 24. In the area defined between the opposing edges 24a, 24a of the side sheets 24, 24, the liquid-permeable topsheet 23 is exposed externally. The overlap between this area and the liquid-absorbent layer 22 is called "main liquid-absorbent region."

X1 shown in FIG. 2 represents a vagina-facing reference line, and this vagina-facing reference line X1 is spaced 100 to 200 mm, preferably 100 to 140 mm, for example, about 120 mm, rearward from the front edge 4 of the napkin body 2.

The vagina-facing reference line X1 as used herein is a target position with which the center of the vaginal opening is to almost coincide when wearing the sanitary napkin 1 along with an undergarment. Leading to this target is through the contour of the sanitary napkin as viewed from the body surface side or the whole design including the arrangement of compression lines on the body surface. Particularly when the fold-back flaps 7, 7 are provided as in the present embodiment, the target usually coincides with the longitudinal centers of the fold-back flaps 7, 7. In the present embodiment, the line passing through the longitudinal centers of the fold-back flaps 7, 7 is taken as the vagina-facing reference line X1.

X2 shown in FIG. 2 represents an anus-facing reference line, and this anus-facing reference line X2 is intended to face the anus when the vagina-facing reference line X1 coincides with the center of the vaginal opening. The anus-facing reference line X2 is usually spaced a distance L2 of 30 to 70 mm, which varies depending on the wearer's body, rearward from the vagina-facing reference line X1.

X3 shown in FIG. 2 represents a coccyx-facing reference line. This coccyx-facing reference line X3 is intended to face the coccyx when the vagina-facing reference line X1 coincides with the center of the vaginal opening. The coccyx-facing reference line X3 is usually spaced a distance L3 of 120 to 180 mm, which varies depending on the wearer's body, rearward from the vagina-facing reference line X1. For example, the coccyx-facing reference line X3 may be spaced 175 mm rearward from the vagina-facing reference line X1. The rear edge 5 of the napkin body 2 and the rear edge 22b of the liquid-absorbent layer 22 are located behind the coccyx-facing reference line X3.

Between the vagina-facing reference line X1 and the coccyx-facing reference line X3, the napkin body 2 is intended to face the vaginal opening, the anus, and the intergluteal cleft. Throughout the disclosure, the cleft extending from forward of the vaginal opening to adjacent the coccyx in the woman's body is merely called "cleft", while the cleft extending from the anus to the coccyx is called "intergluteal cleft".

The backsheet 21 may be a film, for example, a polyethylene resin film having a basis weight of about 23.5 $g/m^2$, and is preferably permeable to moisture. The liquid-absorbent layer 22 may be a mixture of fluff pulp and super absorbent polymer (SAP) wrapped in a hydrophilic tissue having a basis weight of 18 $g/m^2$. The fluff pulp may have a weight of about 400 $g/m^2$; the SAP may have a weight of about 12 $g/m^2$. The side sheet 24 may be a spunbonded nonwoven fabric made of polyethylene/polypropylene sheath/core bicomponent fibers. The spunbonded nonwoven fabric may have a basis weight of about 22 $g/m^2$.

The topsheet 23 may be a through-air bonded nonwoven fabric having a basis weight of about 25 $g/m^2$. The through-air bonded nonwoven fabric may be made of polyethylene/polyethylene terephthalate sheath/core bicomponent fibers with an inorganic filler such as titanium oxide mixed into the core of polyethylene terephthalate.

The surface element 3 may have a hydrophilic, liquid-permeable sheet 31. The liquid-permeable sheet 31 may be a laminate of first and second liquid-permeable sheets 31a, 31b. As shown in FIG. 3, the first liquid-permeable sheet 31a is an outermost layer, while the second liquid-permeable sheet 31b is located inside the first liquid-permeable sheet 31a. In order not to interfere with liquid passage, the first and second liquid-permeable sheets 31a, 31b may be bonded to each other through a hot-melt type adhesive which is applied in a dot pattern, a spiral pattern, or a striped pattern or sprayed in an emulsion state. Alternatively, the first and second liquid-permeable sheets 31a, 31b may be fusion-bonded to each other to have dot-like embossments arranged in such a density as not to interfere with liquid passage.

The first and second liquid-permeable sheets 31a, 31b may each be a through-air bonded nonwoven fabric having a basis weight of about 25 $g/m^2$. The through-air bonded nonwoven fabric may be made of polyethylene/polyethylene terephthalate sheath/core bicomponent fibers with an inorganic filler such as titanium oxide mixed into the core of polyethylene terephthalate.

The first and second liquid-permeable sheets 31a, 31b are not limited to the above-mentioned through-air bonded nonwoven fabric. For example, there may be used a point-bonded nonwoven fabric, a spunlaced nonwoven fabric, a spunbonded nonwoven fabric, or laminations thereof, such as a spunbonded/meltblown/spunbonded nonwoven fabric. In any nonwoven fabrics, however, the fiber density is preferably 0.12 $g/cm^3$ or less and the basis weight preferably falls within the range of 15 to 60 $g/m^2$ so as to improve liquid-permeability.

Alternatively, the first and second liquid-permeable sheets 31a, 31b may each be a resin film formed with a large number of apertures for liquid passage. If desired, the apertured resin film may be used as the first liquid-permeable sheet 31a, while the nonwoven fabric such as through-air bonded may be used as the second liquid-permeable sheet 31b. The liquid-permeable sheet 31 may be embossed in a dot pattern or corrugated. It is, of course, possible that the liquid-permeable sheet 31 is a single nonwoven fabric.

As shown in FIGS. 3 to 6, the opposite edges of the liquid-permeable sheet 31 are bonded to each other to have a bond 32. This bonding may be adhesive-bonding through a hot-melt type adhesive or fusion-bonding. The bond 32 is located to face the topsheet 23 of the napkin body 2 and extends along the longitudinal centerline Oy.

In the first embodiment, the surface element 3 is bonded to the body surface of the napkin body 2 through a hot-melt type adhesive.

In FIG. 2, the bonding region where the surface element 3 is bonded to the body surface of the napkin body 2 is indicated by hatching for the sake of convenience. In the bonding region, the hot-melt type adhesive may be applied in such a manner as not to interfere with passage of liquid through the topsheet 23. For example, the hot-melt type adhesive may be applied in a spiral pattern, a dot pattern, or a striped pattern or sprayed in an emulsion state.

As shown in FIG. 2, the bonding region may be divided into five regions, in the order from front to rear, a first bonding region 33a, a second bonding region 33b, a third bonding region 33c, a fourth bonding region 33d, and a fifth bonding region 33e. The first bonding region 33a extends rearward from the front edge 4 of the sanitary napkin 1, while the fifth bonding region 33e extends forward from the rear edge 5 of the sanitary napkin 1.

In the first bonding region 33a, the adhesive is applied in the shape of a strip which extends longitudinally with a uniform width. The adhesive application width of the first bonding region 33a is indicated by W1. Also in the second to fifth bonding regions 33b to 33e, the adhesive is applied in the shape of a strip which extends longitudinally with a uniform width. The adhesive application width of the second bonding region 33b is indicated by W2, the adhesive application width of the third bonding region 33c is indicated by W3, the adhesive application width of the fourth bonding region 33d is indicated by W4, and the adhesive application width of the fifth bonding region 33e is indicated by W5.

The adhesive application width may vary stepwise such that W1>W2>W3 and W3<W4<W5. Although W1 is equal to W5 and W2 is equal to W4 in the embodiment shown in FIG. 2, W1 may be different from W5 and W2 may be different from W4. For example, W1 and W5 may be 28 mm, W2 and W4 may be 18 mm, and W3 may be 6 mm. The difference between W1 and W2, the difference between W2 and W3, the difference between W5 and W4, and the difference between W4 and W3 are preferably 5 mm or more, or each difference is preferably 10% or more of the larger one. The difference between W1 and W3 and the difference between W5 and W3 are preferably 10 mm or more, or W3 is preferably 80% or less, more preferably 60% or less, of W1 and W5.

In the first embodiment shown in FIGS. 1 to 6, the individual bonding regions 33a-33e are symmetrical about the longitudinal centerline Oy.

As shown FIG. 2, the boundary between the first and second bonding regions 33a, 33b is located on or near the vagina-facing reference line X1. Alternatively, this boundary may be located slightly forward of the vagina-facing reference line X1. As will be described in detail below, therefore, the surface element 3 forms a projection 41 which is low and wide near the vagina-facing reference line X1. The projection 41 increases in height and decreases in width rearward from the vagina-facing reference line X1.

The boundary between the second and third bonding regions 33b, 33c is located on or near the anus-facing reference line X2. Alternatively, this boundary may be located behind the anus-facing reference line X2. As will be described in detail below, therefore, the projection 41 reaches a maximum height and a minimum width behind the anus-facing reference line X2. This highest portion is intended to face the intergluteal cleft.

The front end of the third bonding region 33c is preferably spaced 30 to 180 mm rearward from the vagina-facing reference line X1. The length of the third bonding region 33c is preferably 30 mm or more.

As shown in FIGS. 3 to 6, the surface element 3 has a central elastic member 34 between the first and second liquid-permeable sheets 31a, 31b. The central elastic member 34 extends on the longitudinal centerline Oy in FIG. 2. The central elastic member 34 may be bonded to the first and second liquid-permeable sheets 31a, 31b through a hot-melt type adhesive.

As shown in FIG. 1, the central elastic member 34 has a front end 34c at the front edge 4 of the sanitary napkin 1. Between the front end 34c and a front connection point (or front footpoint) 34a behind the front end 34c, the central elastic member 34, as well as the liquid-permeable sheet 31, is secured on the body surface of the napkin body 2. The central elastic member 34 has a rear end 34d at the rear edge 5 of the sanitary napkin 1. Between the rear end 34d and a rear connection point (or rear footpoint) 34b forward of the rear end 34d, the central elastic member 34, as well as the liquid-permeable sheet 31, is secured on the body surface of the napkin body 2.

It should be noted that the central elastic member 34 is bonded to the liquid-permeable sheet 31 between the front and rear connection points 34a, 34b. Forward of the front connection point 34a and behind the rear connection point 34b, on the other hand, the central elastic member 34 does not have to be bonded to the liquid-permeable sheet 31. Side elastic members 35, which will be described in detail below, may be bonded to the liquid-permeable sheet 31 in the same manner as described above.

FIG. 3 shows the cross section at the location indicated by (a) in FIGS. 1 and 2. At the location (a), as described above, the central elastic member 34 is secured on the body surface of the napkin body 2, while the liquid-permeable sheet 31 is folded flat on the body surface of the napkin body 2. In this folded state, the side elastic members 35, 35 are located at laterally opposing fold lines 3a, 3a. The side elastic members 35, 35 may be bonded between the first and second liquid-permeable sheets 31a, 31b through a hot-melt type adhesive. Thus, when the surface element 3 is folded flat, as shown in FIG. 3, the side elastic members 35, 35 are parallel to the central elastic member 34 with an equal distance laterally from the central elastic member 34.

The side elastic member 35 has a front end 35c at the front edge 4 of the sanitary napkin 1. Between the front end 35c and a front connection point 35a behind the front end 35c, the side elastic member 35 is secured on the body surface of the napkin body 2. The side elastic member 35 also has a rear end 35d at the rear edge 5 of the sanitary napkin 1. Between the rear end 35d and a rear connection point 35b forward of the rear end 35d, the side elastic member 35 is secured on the body surface of the napkin body 2.

The front connection points 35a of the side elastic members 35 are located behind the front connection point 34a of the central elastic member 34 and on the boundary between the first and second bonding regions 33a, 33b shown in FIG. 2. The rear connection points 35b of the side elastic members 35 are located forward of the rear connection point 34b of the central elastic member 34 and on the boundary between the fourth and fifth bonding regions 33d, 33e shown in FIG. 2.

However, if desired, the front connection point 34a of the central elastic member 34 may be located on the same straight line as the front connection points 35a of the side elastic members 35, and the rear connection point 34b of the central elastic member 34 may be located on the same straight line as the rear connection points 35b of the side elastic members 35.

When no external force is exerted on the sanitary napkin 1, the central elastic member 34 exerts an elastic tension between the front and rear connection points 34a, 34b to draw the front and rear connection points 34a, 34b closer to each other. Likewise, the side elastic member 35 exerts an elastic tension between the front and rear connection points 35a, 35b to draw the front and rear connection points 35a, 35b closer to each other.

As a result, as shown in FIG. 1, the front and rear ends of the napkin body 2 approach each other to concavely curve the body surface of the napkin body 2. Here, the central elastic member 34 moves away from the body surface of the napkin body 2 between the front and rear connection points 34a, 34b, and the side elastic member 35 moves away from the body surface of the napkin body 2 between the front and rear connection points 35a, 35b. Therefore, the liquid-permeable sheet 31 is raised from the body surface of the napkin body 2 by the raised portions of the elastic members 34, 35, forming the hollow projection 41. In the first embodiment, the front and rear connection points 34a, 34b of the central elastic member 34 define front and rear ends of the projection 41, respectively.

Forward of the front connection point 34a of the central elastic member 34, as shown in FIG. 3, the liquid-permeable sheet 31 is secured on the body surface of the napkin body 2 in the folded state, forming a front flat portion 42. Behind the rear connection point 34b of the central elastic member 34, the liquid-permeable sheet 31 is also secured on the body surface of the napkin body 2 in the same folded state as shown in FIG. 3, forming a rear flat portion 43.

The cross section of the projection 41 varies depending on the adhesive application widths W1 to W5 of the first to fifth bonding regions 33a-33e shown in FIG. 2.

FIG. 4 shows the cross section of the projection 41 at the location indicated by (b) in FIGS. 1 and 2. The location (b) lies on the first bonding region 33a and is located behind the front connection point 34a of the central elastic member 34 and forward of the front connection points 35a of the side elastic members 35.

At the location (b), the side elastic members 35, 35 are secured on the body surface of the napkin body 2, defining base ends 44a, 44a of the projection 41. On the other hand, the central elastic member 34 is raised from the body surface of the napkin body 2. Thus, the projection 41 provides an apex 41a along the central elastic member 34. The apex 41a extends on the longitudinal centerline Oy in FIG. 2.

At the location (b), the projection 41 has inclined side wall portions 45a, 45a, which are formed of the liquid-permeable sheet 31 to extend from the apex 41a to the respective base ends 44a, 44a. At the location (b), the opening angle between the side wall portions 45a, 45a is indicated by θ1.

At the location (b), the lateral distance between the base ends 44a, 44a of the projection 41 is almost equal to the adhesive application width W1 of the first bonding region 33a shown in FIG. 2. Thus, the projection 41 is wide. More specifically, since the adhesive application width W1 is large, the height from the body surface of the napkin body 2 to the apex 41a is as small as 5 to 30 mm, preferably 5 to 15 mm.

Here, the opening angle θ1 between the side wall portions 45a, 45a is preferably greater than or equal to 120 degrees and less than 180 degrees.

According to other embodiments, the opening angle θ1 may be 90 degrees or more. In case where the side elastic members 35, 35 are spaced farther from the body surface of the napkin body 2 than the central elastic member 34, the upper limit of the opening angle θ1 may be about 270 degrees, preferably 240 degrees or less.

At the location (b), as shown in FIG. 7, the projection 41 is intended to face the front part of the vagina 51 of the woman's body 50. Here, the vagina 51 refers to an area including the labia majora. Since the projection 41 is wide and low and the opening angle θ1 is large at the location (b), the projection 41 can easily fit on the vagina 51 without exerting an excessive pressure or a local pressure thereon.

FIG. 5 shows the cross section of the projection 41 at the location indicated by (c) in FIGS. 1 and 2. The location (c) is almost at the longitudinal center of the second bonding region 33b shown in FIG. 2 and behind the front connection points 35a of the side elastic members 35.

At the location (c), the lateral distance between base ends 44b, 44b of the projection 41 is almost equal to the adhesive application width W2 of the second bonding region 33b shown in FIG. 2. Here, both the central elastic member 34 and the side elastic members 35 are raised from the body surface of the napkin body 2. Moreover, since the front connection points 35a of the side elastic members 35 are located behind the front connection point 34a of the central elastic member 34, the height from the body surface of the napkin body 2 to the side elastic member 35 is smaller than the height from the body surface of the napkin body 2 to the central elastic member 34.

Thus, the projection 41 provides the apex 41a along the central elastic member 34, and upper side wall portions 45b, 45b formed of the liquid-permeable sheet 31 extend from the apex 41a to the respective side elastic members 35, 35. The upper side wall portions 45b, 45b provide inclined wall surfaces, the lateral distance between which gradually increases toward the napkin body 2. The projection 41 also has lower side wall portions 45c, 45c, which extend from the side elastic members 35, 35 to the base ends 44b, 44b. The lower side wall portions 45c, 45c provide inclined wall surfaces, the lateral distance between which gradually decreases toward the napkin body 2. In FIG. 5, the opening angle between the upper side wall portions 45b, 45b is indicated by θ2.

At the location (c) shown in FIG. 5, i.e., on the second bonding region 33b, the height of the projection 41 from the body surface of the napkin body 2 to the apex 41a is preferably about 15 to 40 mm. On the other hand, the opening angle θ2 is preferably about 100 to 160 degrees.

As shown in FIG. 7, the projection 41 having the cross section shown in FIG. 5 is intended to face the body 50 from adjacent the center of the vagina 51 to adjacent the anus 52. Since the distance between the base ends 44b, 44b at the location (c) is smaller than the distance between the base ends 44a, 44a at the location (b), as shown in FIGS. 4 and 5, the height of the projection 41 from the body surface of the napkin body 2 to the apex 41a becomes larger in FIG. 5 than in FIG. 4. In the woman's body 50, the cleft becomes deeper and narrower from the vagina 51 to the anus 52. Therefore, the projection 41 having the cross section shown in FIG. 5 can easily fit in the cleft from adjacent the center of the vagina 51 to adjacent the anus 52.

FIG. 6 shows the cross section of the projection 41 at the location indicated by (d) in FIGS. 1 and 2. The location (d) is located almost at the longitudinal center of the third bonding region 33c shown in FIG. 2.

At the location (d), the lateral distance between base ends 44c, 44c of the projection 41 is almost equal to the adhesive application width W3 of the third bonding region 33c shown in FIG. 2. Here, the projection 41 has the apex 41a, the upper side wall portions 45b, 45b, and the lower side wall portions 45c, 45c, as in FIG. 5.

However, since the lateral distance between the base ends 44c, 44c at the location (d) is smaller than the lateral distance between the base ends 44b, 44b at the location (c), the height of the projection 41 from the body surface of the napkin body 2 to the apex 41a becomes larger in FIG. 6 than in FIG. 5. In FIG. 6, the opening angle between the upper side wall portions 45b, 45b is indicated by θ3. The opening angle θ3 at the location (d) is smaller than the opening angle θ2 at the location (c).

At the location (d), the height of the projection 41 from the body surface of the napkin body 2 to the apex 41a is preferably about 25 to 60 mm. On the other hand, the opening angle θ3 is preferably about 20 to 90 degrees, more preferably 30 degrees or more.

As shown in FIG. 7, the projection 41 having the cross section shown in FIG. 6 is intended to face the intergluteal cleft behind the anus 52. The cleft becomes much deeper and narrower behind the anus 52. Therefore, the projection 41 having the cross section shown in FIG. 6 can easily find its way into the intergluteal cleft and fit against the skin.

At the location (e) shown in FIGS. 1 and 2, i.e., on the fourth bonding region 33d, the projection 41 has almost the same cross section as at the location (c) shown in FIG. 5. As shown in FIG. 7, the projection 41 on the fourth bonding region 33d is intended to face a relatively shallow rear portion of the intergluteal cleft.

The location (f) shown in FIGS. 1 and 2 is located on the fifth bonding region 33e and forward of the rear connection point 34b of the central elastic member 34. At the location (f), the projection 41 has almost the same cross section as at the location (b) shown in FIG. 4. At the location (g), the liquid-permeable sheet 31 is folded flat to form the rear flat portion 43, which has almost the same cross section as the front flat portion 42 shown in FIG. 3. At the locations (f) and (g), the projection 41 is intended to face the coccyx 53 and its vicinity, as shown in FIG. 7. Since the intergluteal cleft becomes shallow near the coccyx 53, the projection 41 can easily fit against the skin at the locations (f) and (g).

The central and side elastic members 34, 35 may be thread-like materials, for example, polyurethane elastic filaments having a fineness in the range of 420 to 10000 dtex, preferably in the range of 1800 to 8000 dtex. Alternatively, they may be rubber threads, such as of natural rubber or synthetic rubber. If desired, the central and side elastic members 34, 35 may be made by bundling or twisting a plurality of thin elastic filaments. In this case, the respective elastic members may be prepared such that the total fineness of the thin elastic filaments falls within the above range.

Between the front and rear connection points 34a, 34b, the central elastic member 34 is bonded to the first and second liquid-permeable sheets 31a, 31b while being stretched at least 1.2 times, preferably at least 1.5 times the original length. Between the front and rear connection points 35a, 35b, likewise, the side elastic members 35, 35 are bonded to the first and second liquid-permeable sheets 31a, 31b while being stretched at least 1.2 times, preferably at least 1.5 times the original length.

Figure 8:
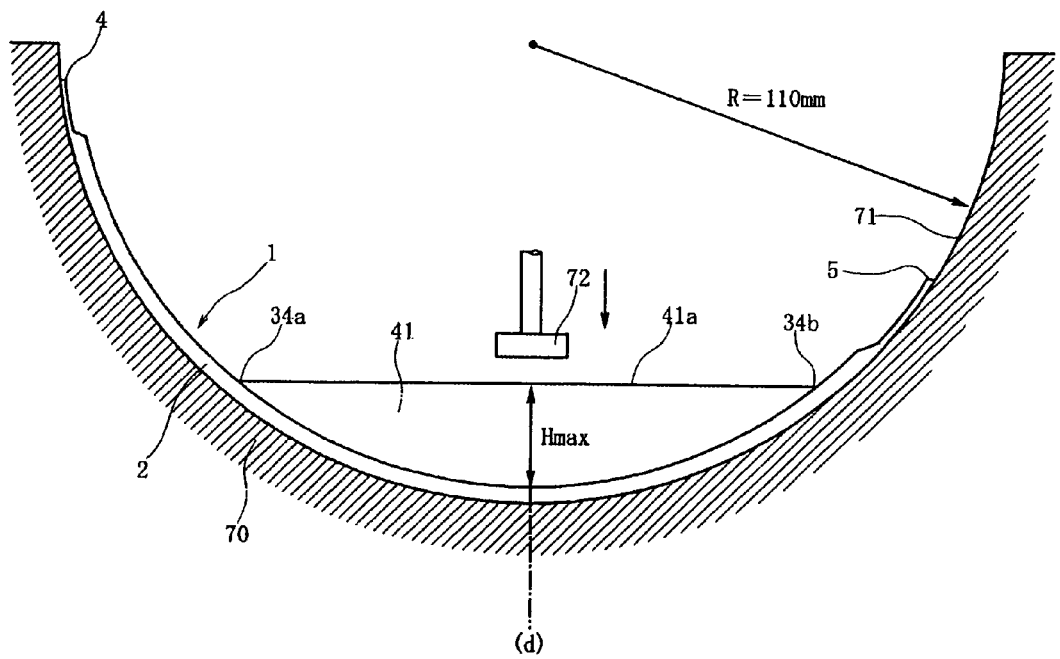
FIG. 8 is a view schematically showing a method for measuring a height and a repulsive force of a projection of a sanitary napkin.

The tension exerted by the central elastic member 34 between the front and rear connection points 34a, 34b may be equal to the tension exerted by each side elastic member 35 between the front and rear connection points 35a, 35b, and is preferably about 0.1 to 5.0 N when the sanitary napkin 1 is flattened. If the tension is below the above range, it will be difficult for the sanitary napkin 1 in a natural state to curve into such a shape as shown in FIG. 1. If the tension is above the above range, a wearer tends to feel uncomfortable. For example, when the sanitary napkin 1 is flattened, the central and side elastic members 34, 35 may each exert a tension of about 0.8 N. When the backsheet 21 of the napkin body 2 is secured on a cylindrical surface 71 having a radius R of 110 mm, as shown in FIG. 8, the central and side elastic members 34, 35 may each exert a tension of about 0.6 N.

Alternatively, the central elastic member 34 may exert a larger tension than the individual side elastic members 35.

The distance between the fold lines 3a, 3a of the flattened surface element 3 (i.e., the width of the front flat portion 42) corresponds to the adhesive application width W1 of the first bonding region 33a, and the width W1 is preferably in the range of 10 to 60 mm. Within this range, the front flat portion 42 shown in FIG. 3 and the projection 41 having the cross section shown in FIG. 4 can sufficiently cover the vagina when come into contact with the vagina.

On the body surface of the napkin body 2, as shown in FIG. 1, there are provided compression lines 61. The compression lines 61 are formed by pressing and heating the topsheet 23 and the liquid-absorbent layer 22 at the same time. The compression lines 61 are laterally spaced from the surface element 3 and extend continuously from the same longitudinal position as or slightly forward of the front connection point 34a of the central elastic member 34 to the same longitudinal position as or slightly behind the rear connection point 34b.

The compression lines 61 function as a stiffening element. With the compression lines 61, the napkin body 2 can be stiffened to resist the elastic contractive force exerted by the elastic members 34, 35. Thus, the napkin body 2 can be prevented from folding between the front and rear connection points 34a, 34b.

As shown in FIGS. 3 to 6, the napkin body 2 has pressure-sensitive adhesive layers 11 on the garment surface of the backsheet 21 for adhesion to an undergarment. The pressure-sensitive adhesive layers 11 extend parallel to and on both sides of the longitudinal centerline Oy. The pressure-sensitive adhesive layers 11 are in the shape of strips and extend the entire length of the napkin body 2.

Although omitted in the drawings, it should be noted that the fold-back flaps 7, 7 and the rear flaps 8, 8 also have pressure-sensitive adhesive layers on the garment surface of the backsheet 21.

FIG. 8 shows a measurement device 70 whose concave cylindrical surface 71 has a radius R of 110 mm. The radius R of 110 mm almost corresponds to the average radius of longitudinal curvature of the cleft of an adult woman who is 27 years old, stands 168 cm tall, weights 56 kg, and has a BMI (body mass index) of 19.8. Here, the BMI is a value obtained by weight (kg)/height(m)$^2$.

The garment surface of the napkin body 2 is fixed on the cylindrical surface 71 through the pressure-sensitive adhesive layers 11 with the longitudinal direction of the sanitary napkin 1 being oriented along a direction of curvature of the cylindrical surface 71. The height of the projection 41 from the body surface of the napkin body 2 to the apex 41a becomes maximum at the location (d) shown in FIGS. 1 and 2, i.e., on the third bonding region 33c. The location (d) is a midpoint between the front and rear connection points 34a, 34b of the central elastic member 34.

The preferred ranges of the height from the body surface of the napkin body 2 to the apex 41a, which have been described hereinabove with reference to FIGS. 3 to 6, can be determined based on values measured radially of the cylindrical surface 71 with the sanitary napkin 1 mounted on the cylindrical surface 71, as shown in FIG. 8.

Furthermore, the repulsive force of the projection 41 may be measured by using a pusher 72 that moves straight radially of the cylindrical surface 71, as shown in FIG. 8. The pusher 72 has a 30 mm diameter circular plane, which is intended to face an object to be pushed. At the location (d), where the rising height of the projection 41 from the body surface of the napkin body 2 becomes a maximum $H_{max}$, the projection 41 is pushed straight by the pusher 72 at a rate of 20 mm/min radially of the cylindrical surface 71.

The force required to depress the projection 41 until the height from the body surface of the napkin body 2 becomes 10 mm is preferably in the range of 0.1 to 5 N, more preferably in the range of 0.3 to 2.0 N. In addition, if the force required to depress the apex 41a of the projection 41 15 mm from the natural state vertically with respect to the cylindrical surface 71 is 0.3 N or more, the apex 41a of the projection 41 at the location (d) can easily reach the deepest part of the intergluteal cleft.

At the location (d), the apex 41a of the projection 41 preferably has a width Wa in the range of 1 to 3 mm. As shown in FIG. 6, the width Wa is measured at the portion containing the central elastic member 34. If the width Wa falls within the above range, the apex 41a of the projection 41 can easily reach the deepest part of the intergluteal cleft.

In the adult woman, the opening angle of the cleft is about 100 degrees near the center of the vaginal opening, about 25 to 35 degrees near the anus, and about 40 to 60 degrees in the rear portion of the intergluteal cleft. Accordingly, if the opening angles θ1, θ2, and θ3 fall within the above ranges, the projection 41 can easily conform to the contours of the woman's body.

When using the sanitary napkin 1, the pressure-sensitive adhesive layers 11 on the garment surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment surfaces of the fold-back flaps 7, 7 are adhered to the outer side of the crotch part. In addition, the pressure-sensitive adhesive layers on the garment surfaces of the rear flaps 8, 8 are adhered to the inner side of the undergarment at a lower part of a back body.

When the sanitary napkin 1 is adhered to the undergarment by a user, the vagina-facing reference line X1 serves as a target for positioning so that it can be worn with the vagina-facing reference line X1 almost coinciding with the longitudinal center of the vagina 51.

As set forth above, since the hollow projection 41 is constructed of the central elastic member 34, the side elastic members 35, and the flexible first and second liquid-permeable sheets 31a, 31b, the cross-sectional shape of the projection 41 can easily be deformed in accordance with the shape of the cleft. Therefore, the projection 41 can easily conform to the contours of the cleft.

Menstrual blood discharged from the vaginal opening passes through spaces between fibers of the liquid-permeable sheets 31a, 31b under force of gravity and is quickly absorbed and retained due to hydrophilicity of the underlying liquid-absorbent layer 22. Although the menstrual blood tends to flow rearward from the vaginal opening during sleep, it can be collected by the projection 41 near or behind the anus 52. The menstrual blood given to the projection 41 passes through or flows down the liquid-permeable sheets 31a, 31b to reach the body surface of the napkin body 2 and is then quickly absorbed and retained by the liquid-absorbent layer 22. Thus, the menstrual blood is effectively prevented from leaking rearward from the sanitary napkin 1.

Hereinbelow, other embodiments of the sanitary napkin according to the present invention will be described. In the following embodiments, the detailed description of the portions having the same construction as those of the first embodiment will be omitted.

Figure 9A:
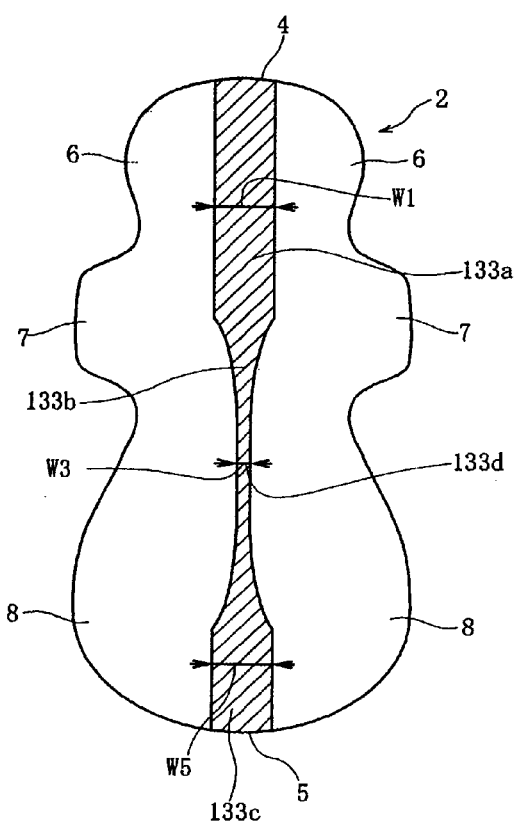
FIGS. 9(A) and 9(B) are plan views showing napkin bodies of modifications of the first embodiment.
Figure 9B:
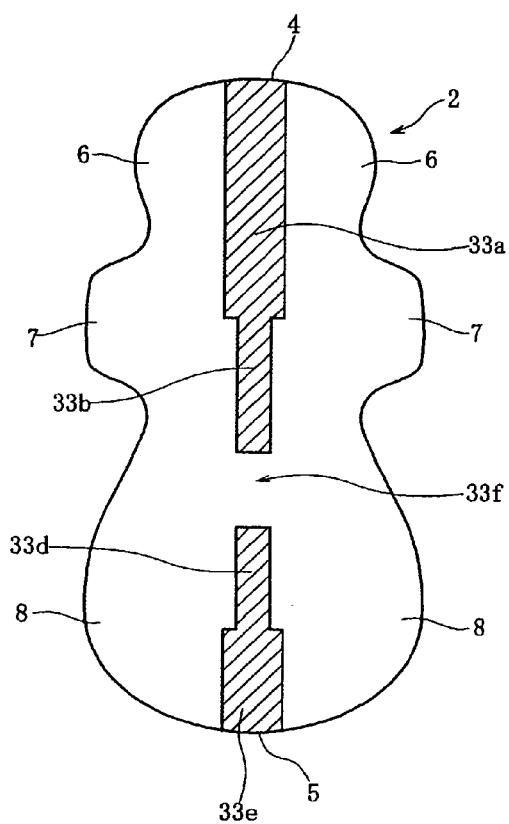

FIGS. 9(A) and 9(B) are plan views showing modifications of the first embodiment, in each of which the napkin body 2 is flattened.

In the modification shown in FIG. 9(A), the bonding region is divided into three regions, in the order from front to rear, a first bonding region 133a, a second bonding region 133b, and a third bonding region 133c. The first bonding region 133a extends rearward from the front edge 4 of the sanitary napkin 1, while the third bonding region 133c extends forward from the rear edge 5.

The first bonding region 133a has the same adhesive application width W1 as the first bonding region 33a shown in FIG. 2. The third bonding region 133c has the same adhesive application width W5 as the fifth bonding region 33e shown in FIG. 2.

In the second bonding region 133b, however, the adhesive application width gradually and continuously decreases toward a location midway between the first bonding region 133a and the third bonding region 133c. In the second bonding region 133b, the location where the width is minimized is indicated by 133d. The location 133d corresponds to the location (d) shown in FIG. 2 and has the same adhesive application width W3 as the third bonding region 33c shown in FIG. 3.

In the modification shown in FIG. 9(A), therefore, the cross section of the projection 41 varies continuously. In more detail, the width gradually decreases and the height gradually increases rearward from the first bonding region 133a. The width is minimized and the height is maximized at the location 133d. Behind the location 133d, the width gradually increases and the height gradually decreases. The projection 41 is intended to face the deepest part of the intergluteal cleft at the location 133d.

In the modification shown in FIG. 9(A), since the lateral distance between the base ends of the projection 41 gradually varies, the surface element 3 hardly peels off the body surface of the napkin body 2.

In the modification shown in FIG. 9(B), the body surface of the napkin body 2 has the first bonding region 33a, the second bonding region 33b, the fourth bonding region 33d, and the fifth bonding region 33e, as in FIG. 2. Between the second bonding region 33b and the fourth bonding region 33d, however, there is provided an unbonding region 33f where no adhesive is applied. The unbonding region 33f extends the same length as the third bonding region 33c shown in FIG. 2.

On the first bonding region 33a, the second bonding region 33b, the fourth bonding region 33d, and the fifth bonding region 33e, therefore, the surface element 3, which is secured on the body surface of the napkin body 2 through the adhesive applied as shown in FIG. 9(B), forms the same flat portions 42, 43 and the same projection 41 as in the first embodiment.

On the unbonding region 33f shown in FIG. 9(B), however, the projection 41, which is high and narrow as shown in FIG. 6, is allowed to move freely on the napkin body 2. Therefore, even if the undergarment is deformed due to movement of the wearer's body and the napkin body 2 is moved laterally, a fit of the projection 41 in the intergluteal cleft can easily be maintained.

In the embodiment shown in FIG. 2, the bonding region is divided into the five regions. However, the second bonding region 33b, the third bonding region 33c, and the fourth bonding region 33d may have an equal adhesive application width, if desired.

The means for securing the surface element 3 on the napkin body 2 is not limited to the hot-melt type adhesive. For example, the surface element 3 may be fusion-bonded to the napkin body 2. In this case, the lateral distance between the base ends of the projection 41 may vary in the same manner as the adhesive application width varies in the foregoing embodiments.

Figure 10:
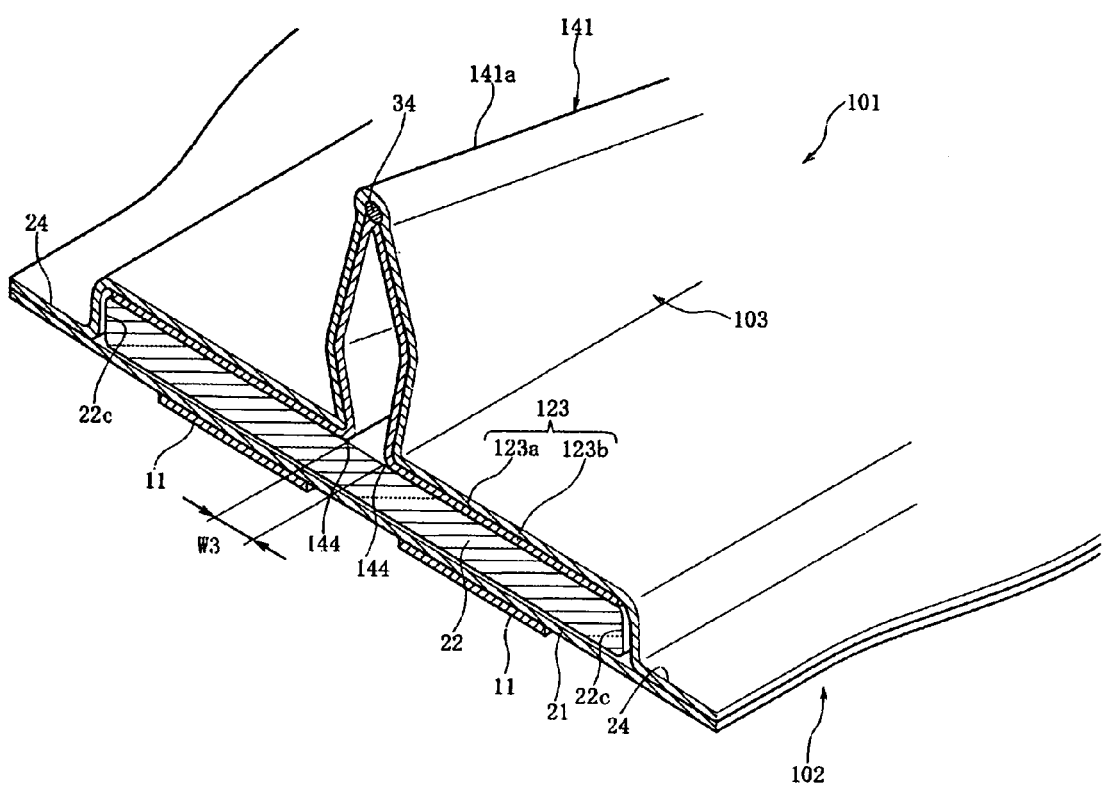
FIG. 10 is a sectional view showing another modification of the first embodiment.

FIG. 10 is a sectional view showing another modification of the first embodiment and corresponding to the sectional view of FIG. 6.

FIG. 10 shows a sanitary napkin 101 comprising a napkin body 102 and a projection 141. The napkin body 102 is covered with a topsheet 123, which is a laminate of first and second liquid-permeable sheet 123a, 123b. The topsheet 123 is bonded to the body surface of the liquid-absorbent layer 22 outside base ends 144, 144 of the projection 141 and to the backsheet 21 outside the side edges 22c, 22c of the liquid-absorbent layer 22.

Between the base ends 144, 144, on the other hand, the topsheet 123 is raised from the body surface of the liquid-absorbent layer 22 to form the projection 141. Thus, a surface element 103 is formed of a part of the topsheet 123. The lateral distance between the base ends 144, 144 may vary with location in the same manner as the adhesive application width varies in FIG. 2, 9(A), or 9(B).

Between the first and second liquid-permeable sheets 123a, 123b, there is disposed and bonded the central elastic member 34. The central elastic member 34 is contained in an apex 141a of the projection 141. If desired, the side elastic members 35 may be provided in the projection 141 shown in FIG. 10.

In the modification shown in FIG. 10, the width and height of the projection 141 may vary in a similar way to the first embodiment shown in FIG. 2 and its modifications shown in FIGS. 9(A) and 9(B). Moreover, since the liquid-absorbent layer 22 is located beneath the projection 141, menstrual blood after passing through the projection 141 can be quickly absorbed by the liquid-absorbent layer 22.

Figure 11A:
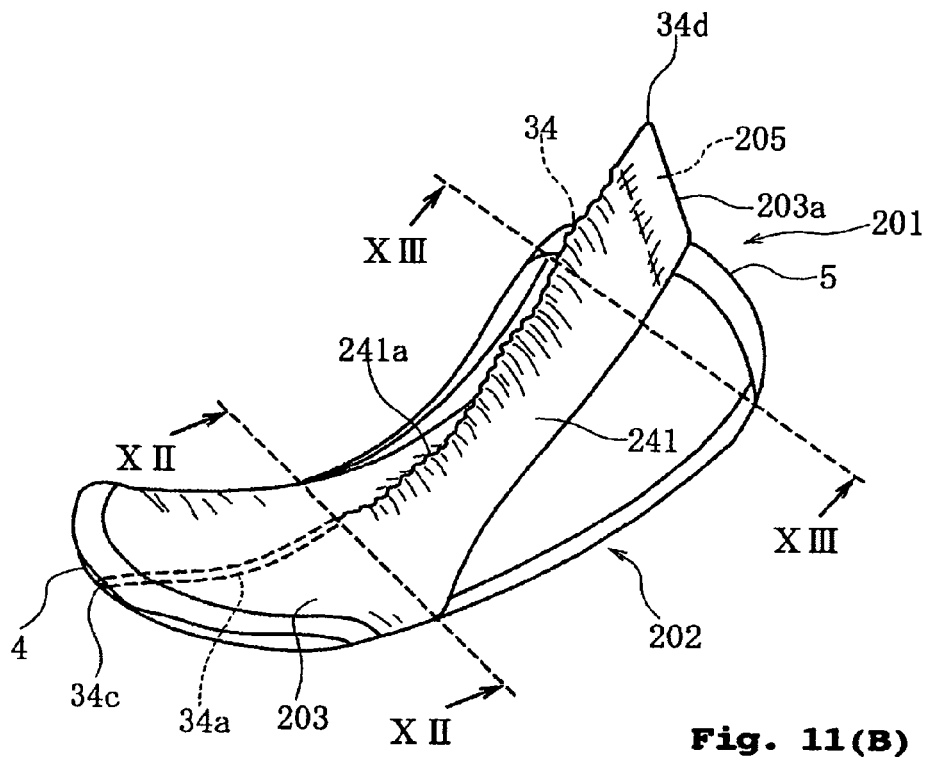
FIG. 11(A) is a perspective view of a sanitary napkin according to a second embodiment of the present invention in a natural state where no external force is exerted thereon.
Figure 11B:
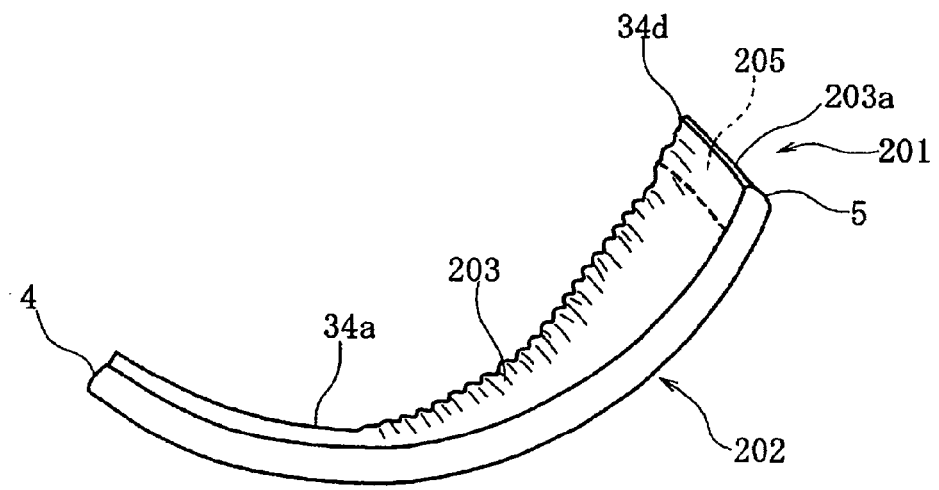
FIG. 11(B) is a side view thereof.
Figure 12:
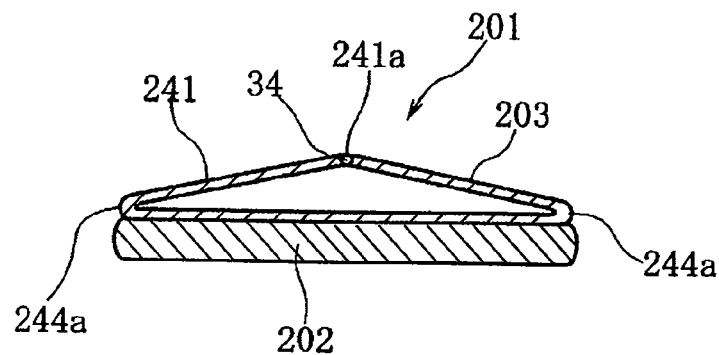
FIG. 12 is a sectional view take along line XII-XII of FIG. 11(A)
Figure 13:
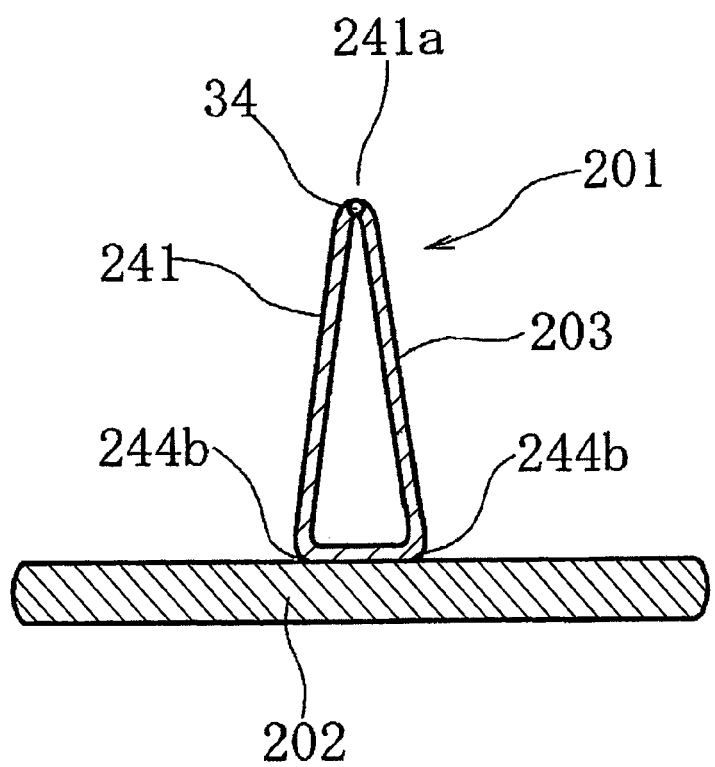
FIG. 13 is a sectional view take along line XIII-XIII of FIG. 11(A)

FIG. 11(A) is a perspective view showing a sanitary napkin 201 according to a second embodiment of the present invention, FIG. 11(B) is a side view of the sanitary napkin 201, FIG. 12 is a sectional view taken along line XII-XII of FIG. 11(A), and FIG. 13 is a sectional view taken along line XIII-XIII of FIG. 11(A).

The sanitary napkin 201 comprises a napkin body 202 and a projection 241 formed of a surface element 203. The napkin body 202 according to the second embodiment has the same construction as the napkin body 2 according to the first embodiment, except that the fold-back flaps 7, 7 are not provided in the napkin body 202.

The surface element 203 includes a liquid-permeable sheet and the central elastic member 34 extending along the longitudinal centerline. Between the front end 34c and the front connection point 34a, the central elastic member 34 is secured on the body surface of the napkin body 202. Behind the front connection point 34a, on the other hand, the central elastic member 34 is separated from the napkin body 202.

The bonding width between the surface element 203 and the napkin body 202 gradually decreases rearward, as shown in FIGS. 12 and 13. The surface element 203 has a reinforcing member 205 at its rear end 203a. The reinforcing member 205 is raised from the napkin body 202. The rear end 203a of the surface element 203 and the rear end 34d of the central elastic member 34 are bonded to the reinforcing member 205. The reinforcing member 205 is preferably hydrophilic and may be made of a material which can be freely deformed when subjected to the weight of a wearer, such as an air-laid pulp, in which pulp (and optionally hydrophilic fibers such as rayon) are compressed and fixed through a binder, a compressed pulp, or a hydrophilic resin foam sheet.

The laterally spaced base ends of the projection 241 are indicated by 244a in FIG. 12 and by 244b in FIG. 13. In the front part of the sanitary napkin 201, the lateral distance between base ends 244a, 244a is large, while the height of an apex 241a, which is raised by an elastic tension of the central elastic member 34, is small. In the rear part of the sanitary napkin 201, on the other hand, the lateral distance between base ends 244b, 244b is small, while the rising height of the apex 241a is large.

In the sanitary napkin 201, since the front portion of the projection 241 is wide and low as shown in FIG. 12, it can easily fit on the vagina and its vicinity; since the rear portion of the projection 241 is narrow and high as shown in FIG. 13, it can easily fit in the intergluteal cleft behind the anus.

Figure 14A:
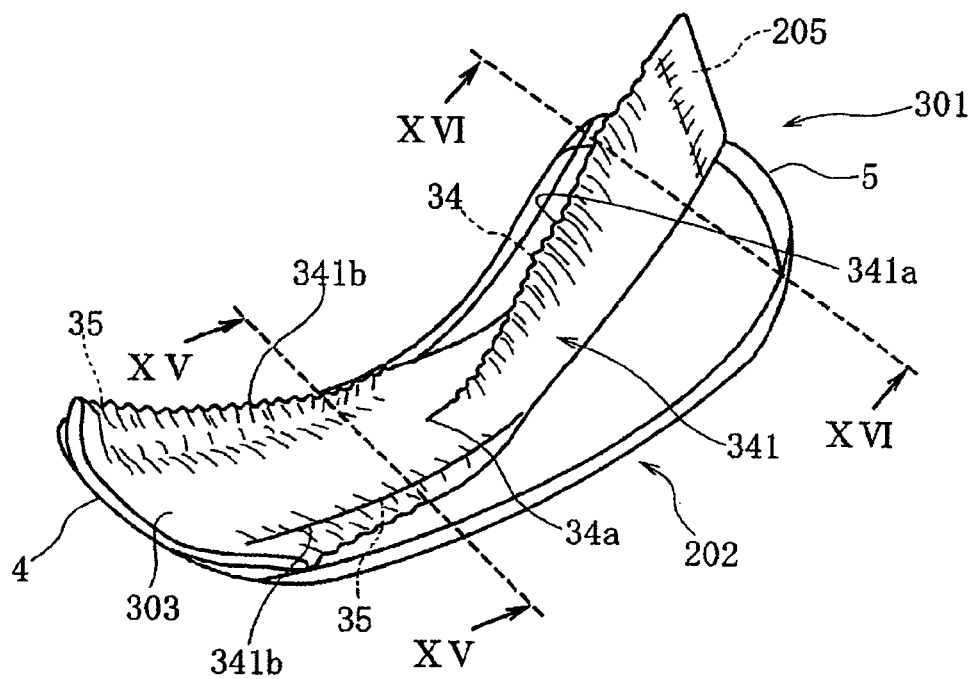
FIG. 14(A) is a perspective view of a sanitary napkin according to a third embodiment of the present invention in a natural state where no external force is exerted thereon.
Figure 14B:
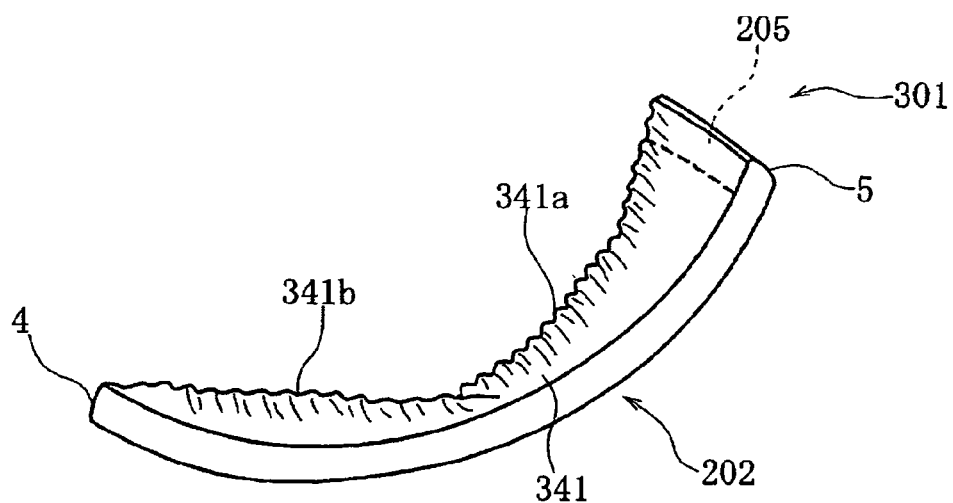
FIG. 14(B) is a side view thereof.
Figure 15:
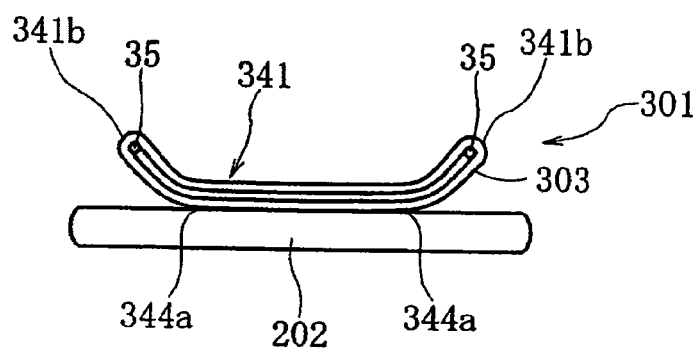
FIG. 15 is a sectional view take along line XV-XV of FIG. 14(A)
Figure 16:
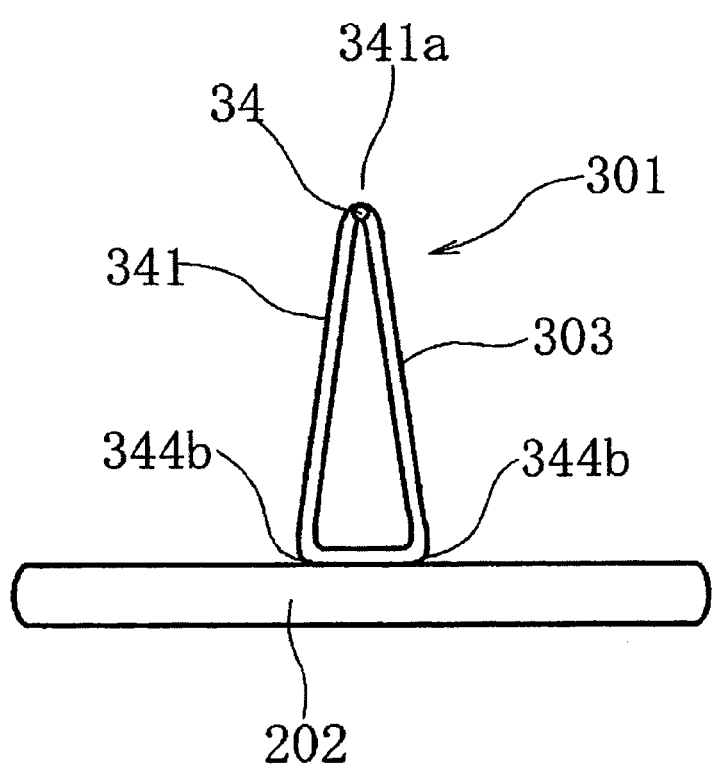
FIG. 16 is a sectional view take along line XVI-XVI of FIG. 14(A)

FIG. 14(A) is a perspective view showing a sanitary napkin 301 according to a third embodiment of the present invention, FIG. 14(B) is a side view of the sanitary napkin 301, FIG. 15 is a sectional view taken along line XV-XV of FIG. 14(A), and FIG. 16 is a sectional view taken along line XVI-XVI of FIG. 14(A).

The sanitary napkin 301 has a surface element 303 on the napkin body 202 that is the same as that of the second embodiment. In its rear portion, the surface element 303 has the same construction as the surface element 203. Thus, the surface element 303 has the reinforcing member 205 which is raised from the napkin body 202 and the central elastic member 34 which is separated from the napkin body 202 and adapted to exert a longitudinal elastic tension between the front connection point 34a and the reinforcing member 205.

In the front portion of the surface element 303, on the other hand, the side elastic members 35, 35 are provided to extend longitudinally near the side edges of the napkin body 202. The side elastic members 35, 35 are bonded to the liquid-permeable sheet of the surface element 303 with their front and rear ends secured on the napkin body 2, so that their intermediate portions under an elastic tension are raised from the napkin body 202.

Moreover, the front portion of the surface element 303 is widely bonded to the napkin body 202, as shown in FIG. 15. The bonding width gradually decreases rearward.

Thus, the surface element 303 forms a projection 341 with three apexes: one central apex 341a and two side apexes 341b, 341b. The laterally spaced base ends of the projection 341 are indicated by 344a in FIG. 15 and by 344b in FIG. 16. In the front part of the sanitary napkin 301, as shown in FIG. 15, the lateral distance between the base ends 344a, 344a is large with the side apexes 341b, 341b extending longitudinally outside the base ends 344a, 344a.

In the rear part of the sanitary napkin 301, as shown in FIG. 16, the lateral distance between the base ends 344b, 344b is small with the central apex 341a being raised high from the body surface of the napkin body 202 under an elastic tension of the central elastic member 34.

Also in the sanitary napkin 301, since the front portion of the projection 341 is wide and low as shown in FIG. 15, it can easily fit on the vagina and its vicinity; since the rear portion of the projection 341 is narrow and high as shown in FIG. 16, it can easily fit in the intergluteal cleft.

Figure 17:
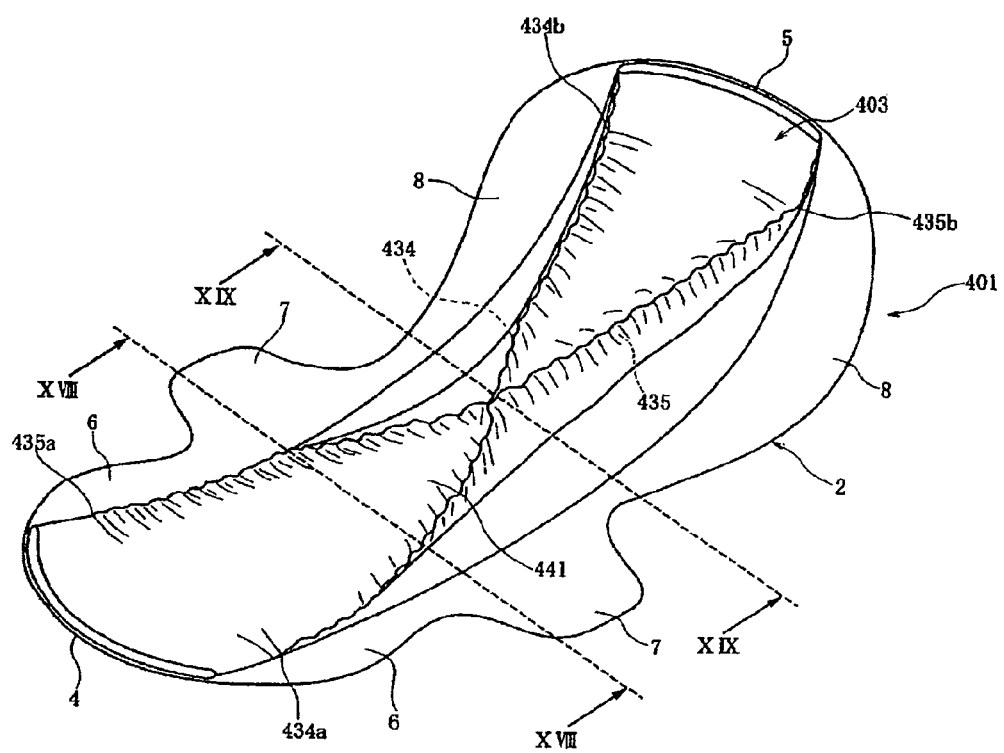
FIG. 17 is a perspective view of a sanitary napkin according to a fourth embodiment of the present invention in a natural state where no external force is exerted thereon.
Figure 18:
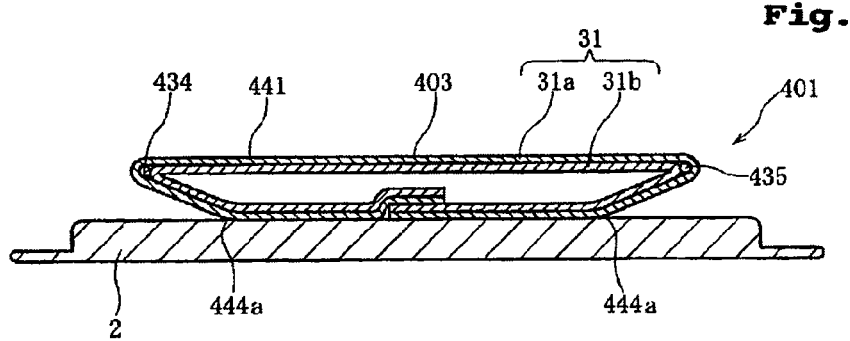
FIG. 18 is a sectional view take along line XVIII-XVIII of FIG. 17.
Figure 19:
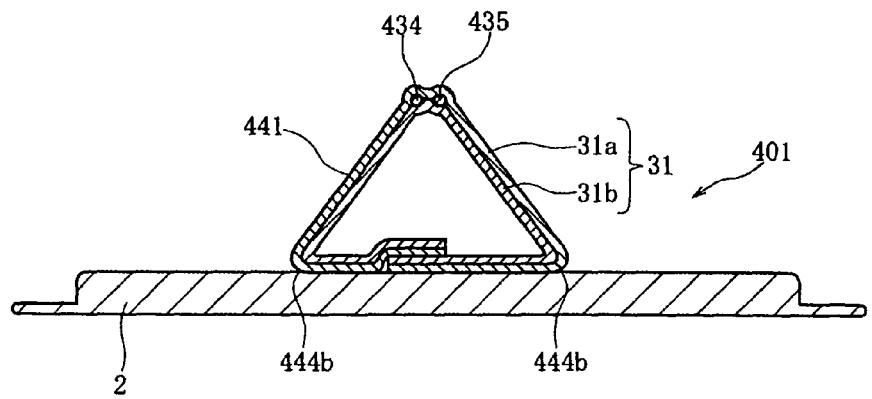
FIG. 19 is a sectional view take along line XIX-XIX of FIG. 17.

FIG. 17 is a perspective view showing a sanitary napkin 401 according to a fourth embodiment of the present invention in a natural state where no external force is exerted thereon, FIG. 18 is a sectional view take along line XVIII-XVIII of FIG. 17, and FIG. 19 is a sectional view take along line XIX-XIX of FIG. 17.

The sanitary napkin 401 has a surface element 403 on the napkin body 2 that is the same as that of the first embodiment. The surface element 403 is formed of the liquid-permeable sheet 31 that is a laminate of the first and second liquid-permeable sheets 31a, 31b, as in the first embodiment. As shown in FIG. 18, the bonding width between the surface element 403 and the napkin body 2 is large in front and rear ends of the sanitary napkin 401 and gradually decreases toward a location midway between the front and rear ends. As shown in FIG. 19, the bonding width is minimized at a location which corresponds to the location (d) shown in FIG. 2.

Between the first and second liquid-permeable sheets 31a, 31b, elastic members 434, 435 are bonded while being stretched at least 1.2 times, preferably at least 1.5 times the original length.

As shown in FIG. 17, the elastic member 434 is raised from the napkin body 2 between front and rear connection points 434a, 434b. The elastic member 435 is also raised from the napkin body 2 between front and rear connection points 435a, 435b. The front connection point 434a of the elastic member 434 and the front connection point 435a of the elastic member 435 are laterally spaced from each other. The elastic members 434, 435 approach each other as they extend rearward and cross each other at the location corresponding to the location (d) shown in FIG. 2. The rear connection point 434b of the elastic member 434 and the rear connection point 435b of the elastic member 435 are laterally spaced from each other in the rear part of the napkin body 2.

The napkin body 2 is curved under an elastic tension exerted by the elastic members 434, 435. Between the front connection points 434a, 435a and the rear connection points 434b, 435b, therefore, the liquid-permeable sheet 31 is raised from the napkin body 2 to form a projection 441.

The laterally spaced base ends of the projection 441 are indicated by 444a in FIG. 18 and by 444b in FIG. 19. In the front part of the sanitary napkin 401, as shown in FIG. 18, since the lateral distance between the base ends 444a, 444a is large and the elastic members 434, 435 are laterally spaced from each other, the height of the projection 441 is small. Also in the rear part of the sanitary napkin 401, the projection 441 has almost the same cross section as in FIG. 18.

The lateral distance between the base ends 444b, 444b of the projection 41 decreases and the height of the projection 41 increases toward the intersection of the elastic members 434, 435. As shown in FIG. 19, therefore, the projection 441 has a generally triangular cross section at the location corresponding to the location (d).

Also in the sanitary napkin 401, since the front and rear portions of the projection 441 are wide and low as in the first embodiment, it can easily fit on the vagina and its vicinity and the coccyx and its vicinity; since the intermediate portion of the projection 441, which is intended to face the intergluteal cleft, is narrow and high and has an acute apex as shown in FIG. 19, it can easily fit in the intergluteal cleft.

Figure 20:
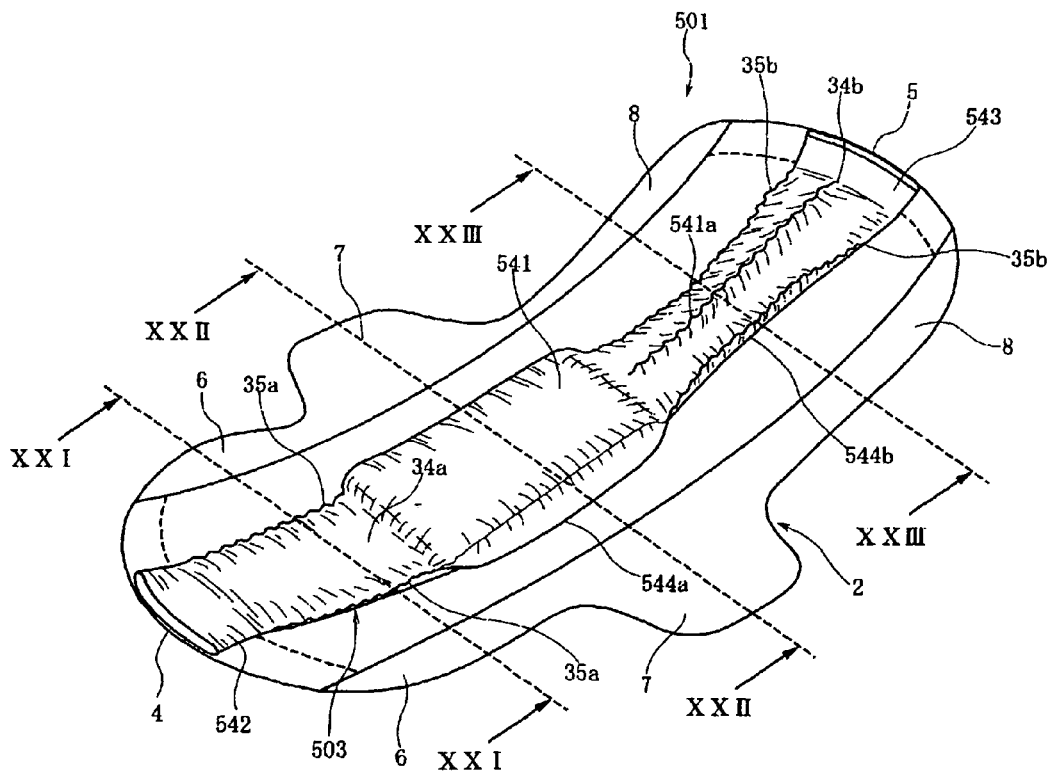
FIG. 20 is a perspective view of a sanitary napkin according to a fifth embodiment of the present invention in a natural state where no external force is exerted thereon.
Figure 21:
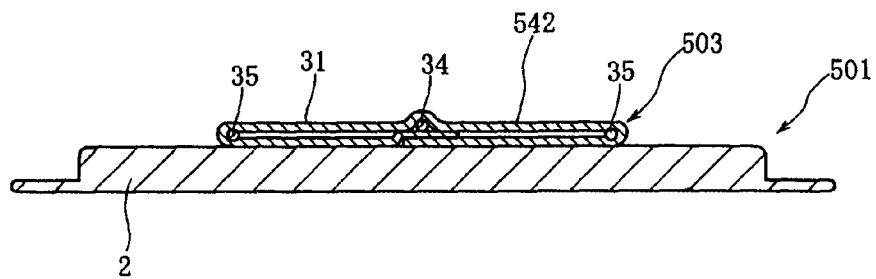
FIG. 21 is a sectional view take along line XXI-XXI of FIG. 20.
Figure 22:
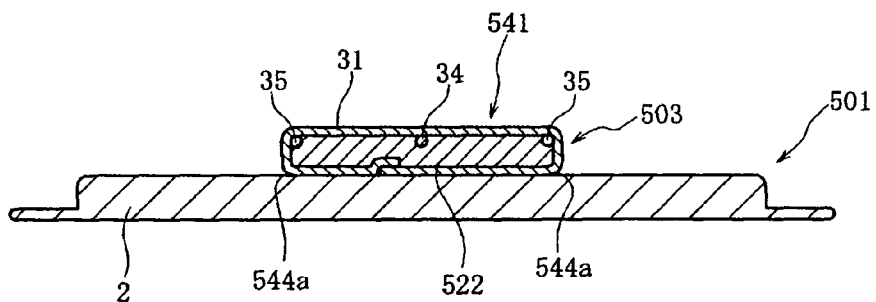
FIG. 22 is a sectional view take along line XXII-XXII of FIG. 20.
Figure 23:
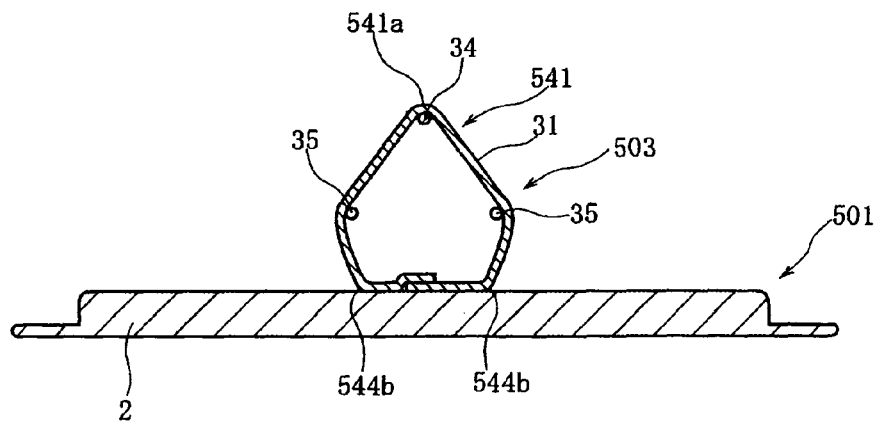
FIG. 23 is a sectional view take along line XXIII-XXIII of FIG. 20.

FIG. 20 is a perspective view showing a sanitary napkin 501 according to a fifth embodiment of the present invention in a natural state where no external force is exerted thereon, FIG. 21 is a sectional view taken along line XXI-XXI of FIG. 20, FIG. 22 is a sectional view taken along line XXII-XXII of FIG. 20, and FIG. 23 is a sectional view taken along line XXIII-XXIII of FIG. 20.

The sanitary napkin 501 has a surface element 503 on the napkin body 2 that is the same as that of the first embodiment. The surface element 503 is formed of the liquid-permeable sheet 31 that is a laminate of the first and second liquid-permeable sheets 31a, 31b, as in the first embodiment. Alternatively, the liquid-permeable sheet 31 may be a singe through-air bonded nonwoven fabric.

The surface element 503 has the central elastic member 34 on the longitudinal centerline and the side elastic members 35, 35 on laterally opposite sides of the longitudinal centerline. As shown in FIG. 20, the front connection point 34a of the central elastic member 34 and the front connection points 35a, 35a of the side elastic members 35, 35 are located slightly forward of the fold-back flaps 7, 7. The rear connection point 34b of the central elastic member 34 is located adjacent the rear edge 5, and the rear connection points 35b, 35b of the side elastic members 35, 35 are located slightly forward of the rear connection point 34b of the central elastic member 34.

Forward of the front connection points 34a, 35a, as shown in FIG. 21, the liquid-permeable sheet 31 of the surface element 503 is folded flat to form a front flat portion 542, which is secured on the body surface of the napkin body 2. Also behind the rear connection point 34b of the central elastic member 34, the liquid-permeable sheet 31 is folded flat to form a rear flat portion 543, as shown in FIG. 20.

Between the front and rear flat portions 542, 543, the surface element 503 forms a projection 541. Behind the front flat portion 542, the bonding width between the surface element 503 and the napkin body 2 is enlarged to house a hydrophilic material 522 in the surface element 503, as shown in FIG. 22. The hydrophilic material 522 may be made of a material capable of absorbing liquid by itself and transferring the liquid to the liquid-absorbent layer 22 of the napkin body 2, such as an air-laid pulp, another pulp layer, or a laminate of hydrophilic nonwoven fabrics or papers. Alternatively, a cushion material may be housed in place of the hydrophilic material 522. The cushion material is a resilient, low-density material which allows liquid such as menstrual blood to descend and transfer to the liquid-absorbent layer 22 under force of gravity, such as a through-air bonded nonwoven fabric.

The laterally spaced base ends of the projection 541 are indicated by 544a in FIG. 22 and by 544b in FIG. 23. At the portion containing the hydrophilic material or cushion material 522, as shown in FIG. 22, the lateral distance between the base ends 544a, 544a is large and the height of the projection 541 is small. The projection 541 is intended to face the vagina and its vicinity at the portion containing the hydrophilic material or cushion material 522.

Behind the fold-back flaps 7, 7, the surface element 503 is hollow, and the bonding width between the surface element 503 and the napkin body 2 is smaller than in FIG. 22. Therefore, as shown in FIG. 23, the lateral distance between the base ends 544b, 544b is small, and an apex 541a of the projection 541 is raised high from the napkin body 2 under an elastic tension exerted by the central elastic member 34.

In the sanitary napkin 501, the projection 541 can fit on the vagina and its vicinity at the wide and low portion containing the hydrophilic material or cushion material 522. This portion feels soft to the touch due to the presence of the hydrophilic material or cushion material 522. On the other hand, the projection 541 can easily fit in the intergluteal cleft at the narrow, elongated, hollow portion shown in FIG. 23.

Figure 24:
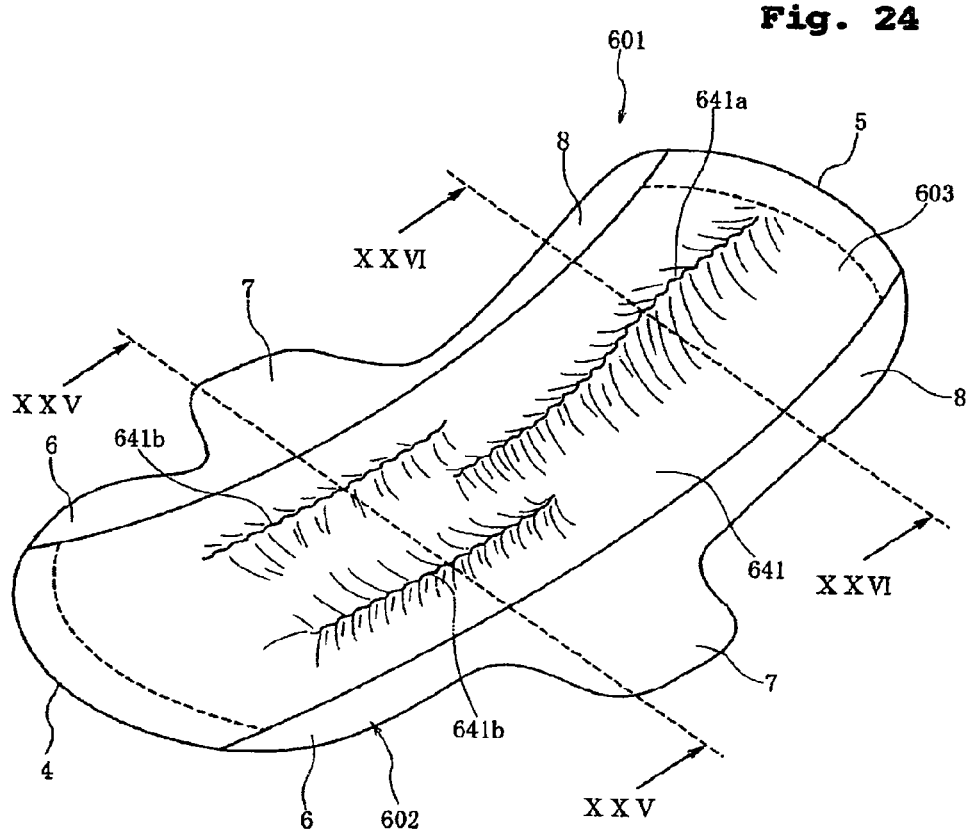
FIG. 24 is a perspective view of a sanitary napkin according to a sixth embodiment of the present invention in a natural state where no external force is exerted thereon.
Figure 25:
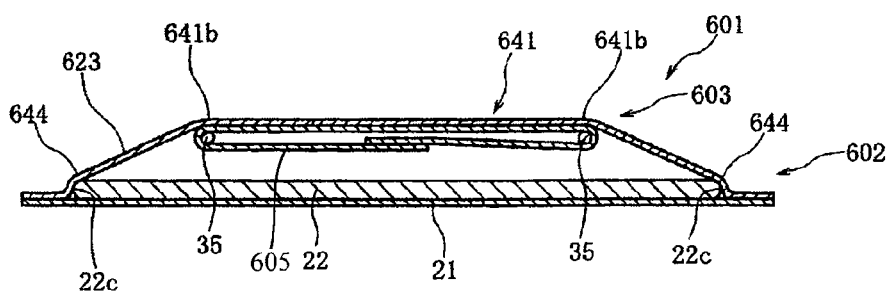
FIG. 25 is a sectional view take along line XXV-XXV of FIG. 24.
Figure 26:
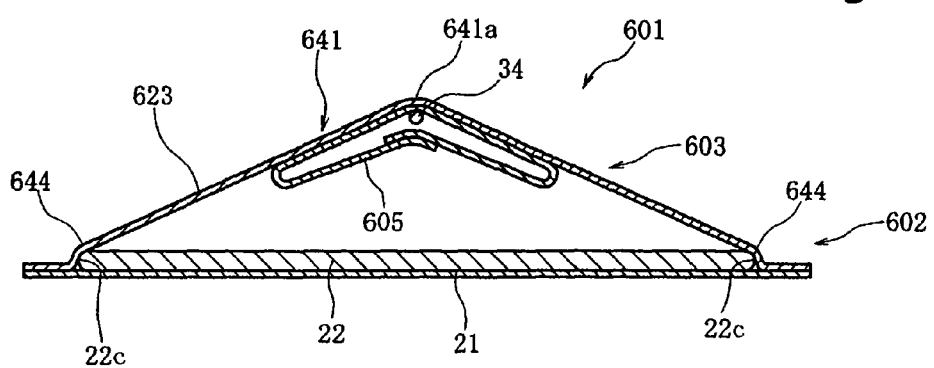
FIG. 26 is a sectional view take along line XXVI-XXVI of FIG. 24.

FIG. 24 is a perspective view showing a sanitary napkin 601 according to a sixth embodiment of the present invention in a natural state where no external force is exerted thereon, FIG. 25 is a sectional view taken along line XXV-XXV of FIG. 24, and FIG. 26 is a sectional view taken along line XXVI-XXVI of FIG. 24.

The sanitary napkin 601 comprises a napkin body 602 and a projection 641 formed of a surface element 603. As shown in FIGS. 25 and 26, the napkin body 602 has the backsheet 21, the liquid-absorbent layer 22, and a topsheet 623. At the front and rear edges 4, 5, the topsheet 623 is bonded to the body surface of the liquid-absorbent layer 22. Aside from the front and rear edges 4, 5, the topsheet 623 is bonded to the side edges 22c, 22c of the liquid-absorbent layer 22 and to the backsheet 21 outside the side edges 22c, 22c, but remains unbonded to the body surface of the liquid-absorbent layer 22. Thus, the topsheet 623 is allowed to move away from the body surface of the liquid-absorbent layer 22.

In the front part of the sanitary napkin 601, the side elastic members 35, 35 are disposed to extend a given length in the longitudinal direction, as shown in FIG. 25. The side elastic members 35, 35, which are laterally spaced from each other, are adapted to exert a longitudinal elastic contractive force between front and rear connection points to move away from the body surface of the liquid-absorbent layer 22. Thus, the projection 641 has side apexes 641b, 641b along the side elastic members 35, 35.

In the rear part of the sanitary napkin 601, the central elastic member 34 is disposed to extend on the longitudinal centerline. The side elastic members 35, 35 lie on laterally opposite sides of a front part of the central elastic member 34. The central elastic member 34 is adapted to exert a longitudinal elastic contractive force between front and rear connection points to move away from the body surface of the liquid-absorbent layer 22. In the rear part of the sanitary napkin 601, therefore, the projection 641 has a central apex 641a along the central elastic member 34.

As shown in FIGS. 25 and 26, a reinforcing sheet 605 is disposed on the garment surface of the topsheet 623 to cover both the central elastic member 34 and the side elastic members 35. The reinforcing sheet 605 may be stiff and made of a hydrophilic or liquid-permeable material, such as an air-laid pulp, an apertured resin film, a paper material, or a through-air bonded nonwoven fabric.

With the reinforcing sheet 605, the topsheet 623 can easily be kept flat between the side apexes 641b, 641b in the front part of the sanitary napkin 601, as shown in FIG. 25. In the rear part, on the other hand, two slopes on both sides of the central apex 641a can easily be kept flat, as shown in FIG. 26.

Throughout the length of the sanitary napkin 601, laterally spaced base ends 644, 644 of the projection 641 are located on the side edges 22c, 22c of the liquid-absorbent layer 22. Thus, the lateral distance between the base ends 644, 644 does not vary at all. However, since the projection 641 is wide and low at the portion having the side elastic members 35, 35, as shown in FIG. 25, it can easily fit on the vagina and its vicinity. In addition, since the apex 641a of the projection 641 is raised high and makes an angle behind the fold-back flaps 7, 7, as shown in FIG. 26, it can easily fit in the intergluteal cleft behind the anus.

In the foregoing embodiments, the projection is provided with at least one elastic member, such as an elastic filament, so as to raise the liquid-permeable sheet of the surface element from the body surface of the napkin body. However, the elastic member is not limited to such an elastic filament. For example, the elastic member may be in the form of a strip. Alternatively, the liquid-permeable sheet of the surface element itself may be adapted to exert an elastic contractive force, without providing the foregoing central and side elastic members. In this case, for example, the liquid-permeable sheet may be a stretchable nonwoven fabric or a nonwoven fabric containing elastic filaments.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:

a napkin body and a surface element fixed to a body faceable surface of the napkin body, the napkin body having front and rear edges and opposing side edges, and a longitudinal center line running from the front edge to the rear edge, the napkin body comprising a liquid-absorbent layer;

a liquid permeable topsheet covering a body faceable surface of the liquid-absorbent layer; and a liquid-blocking backsheet on a garment faceable surface of the liquid absorbent layer, the surface element comprising:

a liquid permeable sheet having front and rear edges and opposing side edges and a constant width in a lateral direction; and a central elastic member bonded to a longitudinal center line of the liquid permeable sheet;

wherein the opposing side edges of the liquid-permeable sheet are overlapped and bonded directly to one another to form a seam which is opposite the longitudinal center line of the liquid permeable sheet;

wherein the seam of the surface element is situated along the longitudinal center line of the napkin body and the surface element is bonded to the napkin body at a plurality of bonding regions of the napkin body along the longitudinal center line of the napkin body, each bonding region having a bonding width that extends laterally in a direction perpendicular to the longitudinal centerline of the napkin body;

wherein the surface element, including the central elastic member, is secured on the body faceable surface of the napkin body in a folded state at both front and rear portions of the napkin body along the longitudinal direction of the napkin body, forming front and rear flat portions of the surface element and wherein, in portions of the surface element between the front and rear flat portions, the central elastic member is adapted to exert a contractive force between the front and rear portions of the napkin body such that the longitudinal center line of the surface element is raised above the body faceable surface of the napkin body to form a hollow projection between the front and rear portions of the napkin body;

wherein a distance between base ends of a bonding region configured to face an area between the vagina and the anus of the wearer is larger than a distance between base ends of a bonding region configured to face the intergluteal cleft of the wearer; and wherein a height of the hollow projection, defined as a height from the topsheet to the elastic member, decreases as the distance between base ends of the bonding regions increases.

2. The sanitary napkin of claim 1, wherein a distance between base ends of a bonding region at a middle portion of the napkin body is smaller than distances between base ends of bonding regions at the front and rear portions of the napkin body.

3. The sanitary napkin of claim 2, wherein a distance between base ends of a bonding region between the front and rear portions of the napkin body varies gradually along the bonding region.

4. The sanitary napkin of claim 1, wherein a distance between base ends of a bonding region between the front and rear portions of the napkin body varies gradually along the bonding region.

5. The sanitary napkin of claim 1, wherein the central elastic member is adapted to exert a longitudinal elastic contractive force to draw front and rear ends of the napkin body closer to each other and concavely curve the body faceable surface of the napkin body.

6. The sanitary napkin of claim 1, wherein the liquid permeable sheet is a laminate of first and second liquid permeable sheets, and the central elastic member is bonded between the first and second liquid permeable sheets.

7. The sanitary napkin of claim 1, wherein:
two side elastic members are secured to the liquid-permeable sheet at positions that are equidistant from the central elastic member, and
wherein a lateral distance between the side elastic members varies longitudinally along the projection between the front and rear portions of the napkin body, and the height of the hollow projection decreases with an increasing lateral distance between the side elastic members.

8. The sanitary napkin of claim 7, wherein each of the central elastic member and the side elastic members have front and rear connection points and wherein the elastic members are fixed to the body faceable surface of the napkin body between the front end of the napkin body and the front connection point of the member, and between the rear end of the napkin body and the rear connection point of the member, and wherein the front connection points of the side elastic members are located rearward of the front connecting point of the central elastic member and wherein the rear connection points of the side elastic members are located forward of the rear connection point of the central elastic member.

* * * * *